US008652525B2

(12) United States Patent
Moses et al.

(10) Patent No.: US 8,652,525 B2
(45) Date of Patent: Feb. 18, 2014

(54) NSAID DELIVERY FROM POLYARYLATES

(75) Inventors: Arikha Moses, New York, NY (US);
Fatima Buevich, Highland Park, NJ (US); Satish Pulapura, Bridgewater, NJ (US); Arvind Viswanathan, Karnataka (IN)

(73) Assignee: TYRX, Inc., Monmouth Junction, NJ (US)

( * ) Notice: Subject to any disclaimer, the term of this patent is extended or adjusted under 35 U.S.C. 154(b) by 299 days.

(21) Appl. No.: 12/499,399

(22) Filed: Jul. 8, 2009

(65) Prior Publication Data

US 2010/0015237 A1 Jan. 21, 2010

Related U.S. Application Data

(60) Provisional application No. 61/079,767, filed on Jul. 10, 2008.

(51) Int. Cl.
*A61K 9/14* (2006.01)
*A61K 31/19* (2006.01)

(52) U.S. Cl.
USPC ............................ 424/489; 514/569; 514/570

(58) Field of Classification Search
None
See application file for complete search history.

(56) References Cited

U.S. PATENT DOCUMENTS

| | | | |
|---|---|---|---|
| 4,428,932 A | 1/1984 | Overell | |
| 5,099,060 A | 3/1992 | Kohn et al. | |
| 5,216,115 A * | 6/1993 | Kohn et al. | 528/176 |
| 5,317,077 A | 5/1994 | Kohn et al. | |
| 5,587,507 A | 12/1996 | Kohn et al. | |
| 5,658,995 A | 8/1997 | Kohn et al. | |
| 5,670,602 A | 9/1997 | Kohn et al. | |
| 6,048,521 A | 4/2000 | Kohn et al. | |
| 6,120,491 A | 9/2000 | Kohn et al. | |
| RE37,160 E | 5/2001 | Kohn et al. | |
| 6,319,492 B1 | 11/2001 | Kohn et al. | |
| RE37,795 E | 7/2002 | Kohn et al. | |
| 6,475,477 B1 | 11/2002 | Kohn et al. | |
| 6,600,010 B2 | 7/2003 | Mao et al. | |
| 6,602,497 B1 | 8/2003 | Kohn et al. | |
| 6,852,308 B2 | 2/2005 | Kohn et al. | |
| 7,056,493 B2 | 6/2006 | Kohn et al. | |
| 7,090,859 B2 * | 8/2006 | Haas | 424/400 |
| 2002/0151668 A1 | 10/2002 | James et al. | |
| 2003/0138488 A1 | 7/2003 | Kohn et al. | |
| 2003/0216307 A1 | 11/2003 | Kohn et al. | |
| 2004/0254334 A1 * | 12/2004 | James et al. | 528/310 |
| 2005/0165203 A1 | 7/2005 | Kohn et al. | |
| 2006/0171990 A1 * | 8/2006 | Asgari | 424/426 |
| 2007/0275027 A1 * | 11/2007 | Wen et al. | 424/422 |
| 2008/0128315 A1 | 6/2008 | Buevich et al. | |

FOREIGN PATENT DOCUMENTS

| | | |
|---|---|---|
| WO | 9952962 A1 | 10/1999 |
| WO | 0149249 A2 | 7/2001 |
| WO | 0149311 A1 | 7/2001 |
| WO | 03091337 A1 | 11/2003 |

OTHER PUBLICATIONS

Young, "International Search Report" from PCT/US2009/049933, 2 pages, United Sates Patent and Trademark Office, Alexandria, Virginia (mailed Aug. 27, 2009).
Young, "Written Opinion of the International Searching Authority" from PCT/US2009/049933, 4 pages, United Sates Patent and Trademark Office, Alexandria, Virginia (mailed Aug. 27, 2009).
Ben-David et al., "Comparison of i.m. and local infiltration of ketorolac with and without local anaesthetic", British Journal of Anaesthesia 1995; 75: 409-412.
Bodanszky, "The Practice of Peptide Synthesis", vol. 21, (SpringerVerlag, New York, 1984).
Bosek et al., "Comparison of analgesic effect of locally and systemically administered Ketorolac in Mastectomy patients", Annals of Surgical Oncology, vol. 3, No. 1, 1996, pp. 62-66.
Brocchini et al., "A combinatorial approach for polymer design", 1997, J. Amer. Chem. Soc. 119:4553-4554.
Curatolo, Michele, "Drug combinations in pain treatment: a review of the published evidence and a method for finding the optimal combination", 2002, Best Practice & Research Clinical Anaesthesiology, vol. 16, No. 4, pp. 507-519.
De Kock et al., "Postoperative analgesic effects of continuous wound infiltration with diclofenac after elective cesarean delivery", Anesthesiology 2007; 106: 1220-1225.
Elias, et al., "Polyesters by Thionyl Chloride activated Polycondensation", Makromol. Chem. 182:681-686, (1981).
Freiberg et al., "Polymer microspheres for controlled drug release", (2004), International Journal of Pharmaceutics 282(1-2) 1-18.
Greenstein et al., "Chemistry of the Amino Acids", (John Wiley & Sons, Inc., New York 1961), p. 929.
Higashi et al., "Direct Polyesterification Promoted by a Complex of Phosphorus Oxychloride with LiCL Monohydrate", 1986, Journal of Polymer Science: PArt A Polymer Chemistry, vol. 24:589-594.
Higashi et al., "Preparation of Aromatic Plyesters by the Direct Polycondensation Reaction with Diphenyl Chlorophosphate in Pyridine", 1983, Journal of Polymer Science: Polymer Chemistry Edition, vol. 21:3241-3247.
Higashi et al., "Preparation of Aromatic Polyesters by Direct Polycondensation with Thionyl Chloride in Pyridine", 1986, Journal of Polymer Science: Polymer Chemistry Edition, vol. 24:97-102.

(Continued)

*Primary Examiner* — David J Blanchard
*Assistant Examiner* — Tigabu Kassa
(74) *Attorney, Agent, or Firm* — Lerner, David, Littenberg, Krumholz & Mentlik, LLP

(57) ABSTRACT

This invention provides biodegradable, sustained-release pharmaceutical compositions of non-steroidal, anti-inflammatory drugs (NSAIDs) formulated with biocompatible, biodegradable tyrosine-derived polyarylates. The compositions are particularly suitable for localized delivery of NSAIDs for various disease states. For example, implantation of the compositions at the site of surgery leads to relatively high local concentrations of the NSAID to reduce or alleviate post-surgical pain. Long term zero order release of certain NSAIDs can also be provided by with certain polymer formulations.

13 Claims, 9 Drawing Sheets

(56) References Cited

OTHER PUBLICATIONS

Higashi et al., "Preparation of Polyaryl Esters by a New Direct Polycondensation Reaction with Arylsulfonyl Chlorides in Pyridine", 1983, Journal of Polymer Science: Polymer Chemistry Edition, vol. 21:3233-3239.

Hooper et al., "Comparative histological evaluation of new tyrosine-derived polymers and poly (L-Lactic acid) as a function of polymer degradation", 1998, J. Biomed. Mat. Res. 41:443-454.

Knudsen et al., "Peritonsillar infiltration with low-dose tenoxicam after tonsillectomy", British Journal of Anaesthesia 1995, 75: 286-288.

Li et al., "Cyclooxygenase-2 increased the angiogenic and metastatic potential of tumor cells", 2002, Biochemical and Biophysical Research Communications 299:886-890.

Lin et al., "Comparison of local infiltration of Tenoxicam and intravenous Tenoxicam for Postoperative analgesia in herniorrhaphy", Acta Anaesthesiol Sin 36:23-29, 1998.

Mikkelsen et al., "Comparison of Tenoxicam by intramuscular injection or wound infiltration for analgesia after inguinal herniorrhaphy", Anesth Analg 1996;83:1239-1243.

Moore et al., "Room temperature Polyesterification", 1990, Macromolecules 23:65-70.

Morton et al., "Nonsteroidal anti-inflammatory drugs and bone mineral density in older women: The rancho Bernardo Study", University of California, San Diego, La Jolla, California, US, Journal of bone and mineral research 1998, vol. 13, No. 12, pp. 1924-1931.

Ogata et al., "Synthesis of polyester by direct polycondensation with hTriphenylphosphine", 1981, Polymer Journal, vol. 13, No. 10, pp. 989-991.

Physicians Desk Reference 1999: 3350-3353.

Pulapura et al., "Structure-property relationships for the design of polyiminocarbonates", 1990, Biomaterials 11:666-678.

Pulapura et al., "Tyrosine-derived polycarbonates: Backbone-modified "Pseudo"-Poly(Amino Acids) designed for biomedical applications", 1992, Biopolymers vol. 32, pp. 411-417.

Romsing et al., "Local infiltration with NSAIDs for postoperative analgesia: evidence for a peripheral analgesic action", Acta Anesthesiol Scand 2000; 44: 672-683.

Tanaka et al., "Synthesis of polyestes by direct polycondensation with Picryl Chloride", 1982, Polymer Journal, vol. 14, No. 8, pp. 643-648.

U.S. Appl. No. 60/375,846, filed Apr. 24, 2002.

Yasuda et al., "Synthesis of Polyester by Direct Polycondensation with Triphenylphosphine", 1983, Journal of Polymer Science: Polymer Chemistry Edition, vol. 21, pp. 2609-2616.

\* cited by examiner

NSAID DELIVERY FROM POLYARYLATES

RELATED APPLICATION

This application claims the benefit of and priority to U.S. provisional application Ser. No. 61/079,767 filed Jul. 10, 2008 in the U.S. Patent and Trademark office, which is hereby incorporated by reference herein in its entirety.

FIELD OF INVENTION

This invention provides biodegradable, sustained-release pharmaceutical compositions of non-steroidal, anti-inflammatory drugs (NSAIDs) formulated with biocompatible, biodegradable tyrosine-derived polyarylates. The compositions are particularly suitable for localized delivery of NSAIDs for various disease states. For example, implantation of the compositions at the site of surgery leads to relatively high local concentrations of the NSAID to reduce or alleviate postsurgical pain. Long term zero order release of certain NSAIDs can also be provided by with certain polymer formulations.

BACKGROUND TO THE INVENTION

The non-steroidal anti-inflammatory drugs (NSAIDs) are the most widely used group of drugs in the history of medicine. Since the introduction of aspirin in 1899, about 20 of these drugs have become available for use in the United States and Europe. They are used for the relief of symptoms of arthritis, for acute musculoskeletal conditions, miscellaneous injuries, and post-operative pain management.

NSAIDs are effective for the management of acute postoperative pain relief. These agents can be used in combination with opioid analgesics and local anesthetics for the relief of severe postoperative pain, where the combination results in reduced narcotic requirements and improved analgesia compared with opioids and/or local anesthetics alone. NSAIDs have been shown to be effective in a wide variety of postoperative pain states, including those following thoracotomy, major orthopedic surgery such as hip arthroplasty, upper and lower abdominal surgery, and minor outpatient surgery. The benefits of combining NSAIDs with opioid analgesics in the immediate post-operative period include not only improved analgesia, but also compounds benefits associated with narcotic sparing (improved respiratory function, reduction in nausea and vomiting, and reduced sedation). It has been suggested that NSAIDs may improve not only the quality but also the speed of recovery. By adding the NSAIDs to a routine analgesic armamentarium, the goal of preventing or eliminating post-operative pain, rather than only reducing post-operative pain, can be achieved.

However, the overall utility of NSAIDs is limited by the need to avoid dose-related side effects and by their mechanism of action. NSAIDs are extensively protein bound (>90%) and their effectiveness varies according to serum albumin and total protein. Some of the potential complications of NSAIDs are untoward effects due to a decrease in synthesis of various beneficial prostaglandins. This may cause a reduction of renal blood flow, especially in patients with heart failure and/or renal insufficiency, lead to gastric mucosal irritation, liver toxicity, and the inhibition of platelet aggregation. These potential complications of NSAIDs have caused clinicians to restrict the dosage of NSAIDs.

While NSAIDs are effective in reducing inflammation and inducing analgesia, the conventional oral dosage forms of these drugs characteristically have short half-lives and irritate the gastric mucosa. A major limitation with the use of NSAIDs is the high prevalence of gastrointestinal irritation. This problem ranges in severity from minor irritation to gastritis, duodenitis, and frank ulcerations with bleeding. The symptoms usually manifest themselves as "pain" or "distress." These symptoms are often so severe and frequent, especially in the elderly, that they result in discontinuing NSAID therapy.

Site-specific (but not sustained release) delivery of NSAIDs has been tested by infiltration of various types of surgical wounds by many groups (Ben-David et al., 1995, Br. J. Anaesth. 75:409-412; Bosek et al., 1996, Ann. Surg. Oncol. 3:62-66; Knudsen et al., 1995, Br. J. Anaesth. 75:286-8; Lin et al., 1998, Acta Anaesth. Sin. 36:23-9; Mikkelsen et al., 1996, Anesth. Analg. 83:1239-43). No prospective randomized trials have been performed to demonstrate that such an approach is effective and limits complications; however, the bulk of evidence supports this site-specific approach. In 2001, a comprehensive review of the literature on the local infiltration of NSAIDs was written by Romsing (Romsing et al., 2001, Acta Anaesthesiol. Scand. 44:672-83), and in 2007, De Kock et. al. published a clinical trial comparing continuous wound infiltration with diclofenac after cesarean delivery and showed that it was more effective than ropivacaine continuous wound infiltration with intravenous (iv) diclofenac.

Romsing reviewed 16 randomized, controlled, double blind trials of site-specific NSAIDs (for a total of 884 patients). The treatments were by intra-articular injection, in intravenous regional anesthesia and wound infiltration (5 studies). The results showed that local delivery of NSAIDs was better than placebo in 4 studies and equal in 1, that local delivery of NSAIDs was better than systemic delivery of NSAIDs in 2 studies and equal in 3, and that, overall, the 24-hour consumption of supplemental analgesics was reduced by 60% by patients receiving local NSAIDs.

The above considerations demonstrate that there is a pressing need for improved products to relieve pain after surgery. There is ample evidence that NSAIDs have a peripheral mode of action. NSAID efficacy may be improved through sustained release and higher local concentration. NSAID safety may be improved through site-specific delivery that minimizes systemic effects and could provide the following advantages constant local analgesia without debilitating breakthrough pain, predictable analgesia since local binding of drug to protein will reduce individual variability in dose-response, avoidance/minimization of the complications of opiates and systemic NSAIDs, and allow patients to be discharged earlier from same-day surgery and return to work more quickly.

There are very few biopolymers in widespread use for the development of sustained release, injectable or implantable formulations of drugs. The most commonly employed resorbable biopolymers are poly(lactic) acid (PLA), poly(glycolic) acid (PGA), copolymers of the two (PLGA), and collagen. Two others are in limited use: polycaprolactone (a component of certain products with regulatory approval only in Europe) and one polyanhydride compound that comprises the Gliadel Wafer® marketed by Guilford Pharmaceuticals.

Lactic and glycolic acid-based polymers are some of the most commonly employed synthetic polymers in the development of drug delivery vehicles for use in humans despite their limitations. The most pressing problem is the drug "burst" that occurs soon after implantation. Most of the drug leaches out of the polymer vehicle within the first 24-48 hours of implantation as a result of incompatibility between drug and polymer. Other significant problems include: drug instability due to the acidic nature of the polymer, formulation techniques that use organic solvents and thus denature proteins and peptides, and site injection irritation of the initial biomaterial. The acidity of the lactic and glycolic acid breakdown products may also be deleterious to cartilage.

The physicochemical properties of the polymer in a sustained release formulation controls the fundamental behavior of the system. Since the number of biodegradable polymers available for drug delivery is very small, and the existing development methods for controlled delivery systems rely heavily on the currently used polymers, most new development work focuses on novel processes or excipients to control drug release profiles from those existing materials. For example, polylactic acid (PLA) (D&L forms), polyglycolic acid (PGA) (D&L forms) are currently the most widely used materials in the development of degradable drug delivery systems. Interestingly, these materials were not developed originally for this application, but rather for manufacturing biodegradable sutures. Since this class of materials has little structural diversity, there is limited room to manipulate drug-polymer interactions and thus to alter release profiles.

Brocchini et al., 1997, J. Amer. Chem. Soc. 119:4553-4554 described a class of polymers known as polyarylates that were formed by the combinatorial synthesis of 14 different tyrosine-derived diphenols with 8 different dicarboxylic acids to give a 112 member library of strictly alternating A-B type copolymers. These polyarylates are biocompatible and biodegradable. The dicarboxylic acids are naturally occurring metabolites like adipic acid and succinic acid. Since the polymers contain an ester linkage in the backbone, they are biodegradable and their degradation products, tyrosine, desaminotyrosine, and the dicarboxylic acids, all have known toxicity profiles. The polymers produce significantly less acid during their degradation process than the PLA and PGA families. Systematic variations in polymer properties can be obtained by varying the nature of the pendant group attached to the C-terminus of the tyrosine diphenol and the methylene groups in the dicarboxylic acid.

SUMMARY OF THE INVENTION

The present invention provides novel compositions of matter comprising a polymer matrix formed by a biodegradable polyarylate polymer in which a non-steroidal anti-inflammatory drug (NSAID) is dispersed, dissolved, or embedded in the matrix. These novel compositions provide superior results as drug delivery devices and overcome many of the problems that have plagued prior art drug delivery devices. Prior art attempts to solve issues related to drug-polymer incompatibility usually focused on the addition of excipients to modulate the release of medicine from these older-type polymers. In the present invention, drug release is controlled by manipulating non-covalent interactions between tyrosine-derived polyarylates and a wide variety of NSAIDs, without the use of excipients. In preferred embodiments, the present invention provides for the delivery of ketoprofen in a bust-free, sustained release fashion for periods ranging from a few days to several weeks or months. In some embodiments, ketoprofen is release can occur with zero order kinetics for a period of up to several months. The compositions and formulations of the invention provide relief of pain following surgery or in other painful conditions.

The compositions of the present invention comprising a tyrosine-derived polyarylate, and an NSAID can be formed into a shape and a size suitable for use as a drug delivery device for the NSAID, where the NSAID is present in an amount suitable to provide analgesia when the drug delivery device is implanted into a patient in need of analgesia. The polyarylates and NSAIDs can be formulated into microspheres, films, rods, sheets and other forms that can function as delivery vehicles capable of long-term, sustained release of NSAIDs. The drug delivery vehicles can be applied locally to soft tissues in the vicinity of a, or directly within, surgical incision or a traumatic wound, thus providing for local delivery of NSAID to the incision or wound. Therefore, the compositions of the present invention could be applied as part of a process for inhibiting post-surgical pain for several days or weeks, which comprises the single administration to the incisional site of surgical trauma of an effective amount of a drug in a biodegradable carrier, including as an active ingredient a non-steroidal anti-inflammatory drug, such administration occurring just prior to surgical closure and continuing for a period of time sufficient to inhibit incisional pain.

In certain embodiments, these delivery vehicles provide a continuous source of NSAIDs for a period of about 2-10 days, preferably about 3-8 days, and even more preferably about 4 days. In other embodiments, sustained drug delivery for even longer periods is possible. In certain embodiments, these delivery vehicles exhibit zero-order release kinetics of the NSAID.

A preferred polyarylate for use in the present invention can be represented by Formula 1

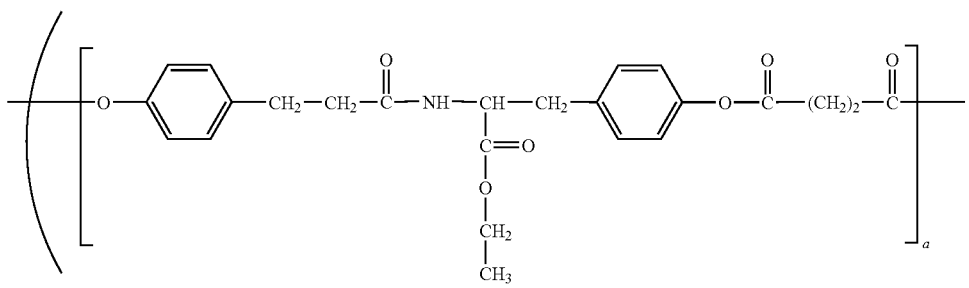

Formula 1

-continued

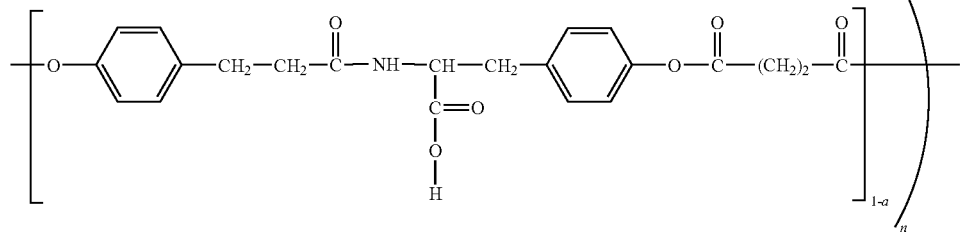

where a is a number between 0.01 and 0.99 that represents the mole fraction of esters in the pendant chains of the polyarylate as compared to the mole fraction of free carboxylic acid groups in the pendant chains. Preferred values of a are: between about 0.50 and about 0.98; between about 0.80 and about 0.97; between about 0.80 and about 0.95; between about 0.85 and about 0.95; and between about 0.90 and about 0.95, Also among the preferred values of a are: about 0.95, about 0.90, about 0.85, about 0.80, about 0.75, about 0.70, and about 0.60. [0017]

A preferred NSAID for use in the present invention is ketoprofen. In one aspect, the invention is directed to a burst-free, sustained-release formulation comprising relative amounts of ketoprofen and a tyrosine-derived polyarylate, which when measured in vitro under physiological conditions at room temperature, are sufficient to release less than about 50% of said ketoprofen within 24 hours and to release ketoprofen for at least 3 to 5 days.

For example, an embodiment wherein said delivery vehicle, when injected once, provided a continuous source of NSAID for 1-3 months, such embodiment would be particularly useful for the prevention of chronic pain such as that caused by osteoarthritis.

BRIEF DESCRIPTION OF THE DRAWINGS

FIG. 10 shows scanning electron microscopy analysis (SEM) of ketoprofen-containing microspheres from LB1 prepared using dry sieving.

DETAILED DESCRIPTION

Figure 1:
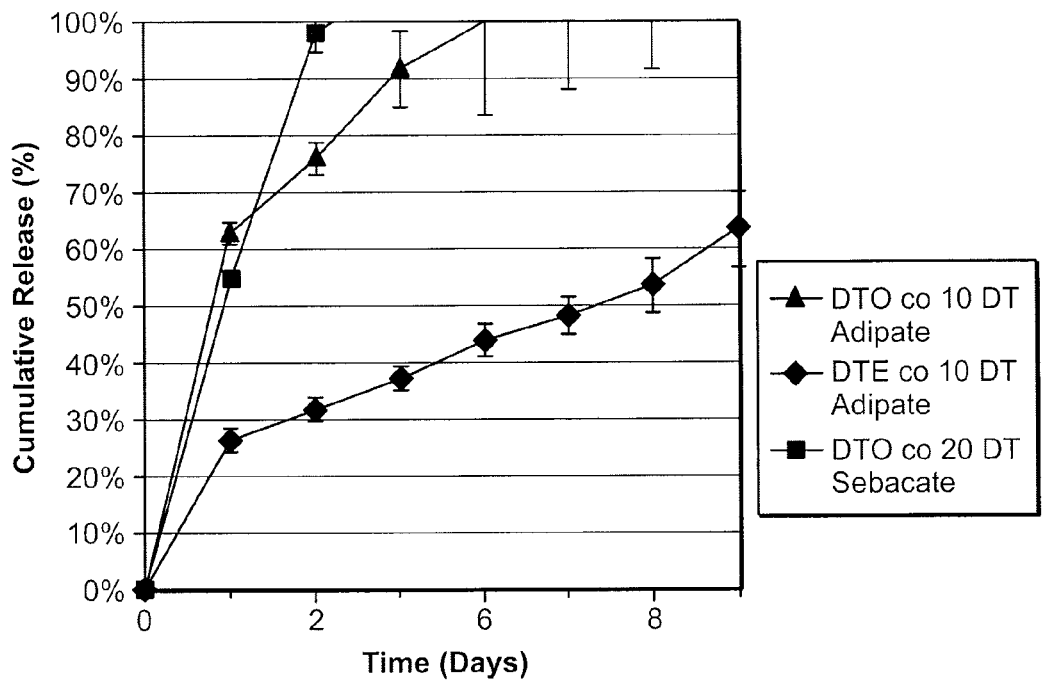
FIG. 1 shows the release of ketoprofen from different fast degrading polyarylates, (♦) for p(10% DT, DTE adipate), (▲) for p(10% DT, DTO adipate and (■) for p(20% DT, DTO sebacate.

For the purpose of describing the present invention:

"Microparticles" are solid particles, generally round, optionally smooth, made from a polyarylate polymer matrix and having a diameter of about 50 μm to about 750 μm. Microparticles can be made by grinding preformulated film as exemplified in Example 3 or by mixing the NSAID and the polymer in a solvent, drying and grinding the dried powder to produce microparticles of the desired size as exemplified in Example 4.

"Microspheres" are solid particles, generally round, optionally smooth, made from a polyarylate polymer matrix and having a diameter of about 50 μm to about 750 μm. Microspheres are made by a standard oil-in-water emulsification methodology or similar method (see, e.g., Freiberg et al. (2004) Int. J. Pharm., 282(1-2) 1-8, "Polymer microspheres for controlled drug release"). The microspheres can be also be dried and ground into a powder to produce microspheres of a desired size. The method described in Example 5 is exemplary.

"Biocompatible" means non-toxic to the mammalian body, and in particular, non-toxic to the human body. "Biocompatible" substances are pharmaceutically acceptable, non-carcinogenic, and are not prone to induce inflammation.

"Biodegradable" refers to a substance that is able to be broken down to its constituent subunits in the mammalian body in a period of time of no more than 2 years, the exact time depending on the amount and nature of the biodegradable substance.

When "percent loading" of an NSAID in a polyarylate polymer matrix is described, such loading refers to percentage by weight, i.e., w/w.

"Physiological conditions" refers to the conditions of temperature, pressure, ionic strength, and salt composition found in the mammalian body or to in vitro systems designed to mimic relevant features of those conditions such as, e.g., the phosphate buffered saline solutions used in the experiments described herein that measured NSAID release rates.

Polyarylates are strictly alternating A-B type copolymers consisting of a diphenol component and a dicarboxylic acid component. The dicarboxylic acids allow for variation in the polymer backbone while the diphenols contain a moiety for appending and varying a pendent chain.

The present invention employs certain polyarylates in which a non-steroidal anti-inflammatory drug (NSAID) has been dispersed, dissolved, or embedded for medical applications. The polyarylates are based upon certain tyrosine-derived monomers, which are co-polymerized with a variety of dicarboxylic acids. The tyrosine-derived monomer can be thought of as a desaminotyrosyl tyrosine dipeptide in which the tyrosine moiety's pendant carboxyl group has been esterified. The structure of one example of a suitable tyrosine-derived monomer is shown in Formula 2.

Formula 2

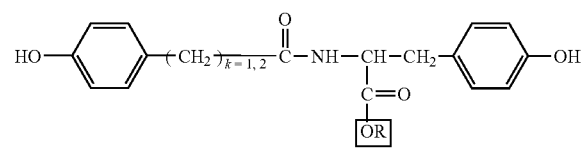

In Formula 2, R is selected from the group consisting of: a straight or branched chain alkyl group containing up to 18 carbon atoms, an alkylaryl group containing up to 18 carbon atoms, a straight or branched chain alkyl group containing up to 18 carbon atoms in which one or more carbon atoms is substituted by an oxygen, and an alkylaryl group containing up to 18 carbon atoms in which one or more carbon atoms is substituted by an oxygen.

In preferred embodiments, R is a straight or branched chain alkyl group containing 2-8 carbon atoms.

In particular embodiments, R is selected from the group consisting of: methyl, ethyl, propyl, butyl, isobutyl, sec-butyl, hexyl, octyl, 2-(2-ethoxyethoxy)ethanyl, dodecanyl, and benzyl.

In preferred embodiments, R is selected from the group consisting of: ethyl, hexyl, and octyl. In an especially preferred embodiment, R is ethyl and k is 2.

One class of polyarylates suitable for use in the present invention is formed by polymerizing the tyrosine-derived monomers of Formula 2 with the diacarboxylic acids of Formula 3.

Formula 3

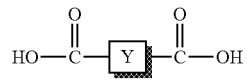

In Formula 3, Y is a saturated or unsaturated, substituted or unsubstituted alkylene, arylene, and alkylarylene group containing up to 18 carbon atoms. The substituted alkylene, arylene, and alkylarylene groups may have backbone carbon atoms replaced by N, 0, or S, or may have backbone carbon atoms replaced by keto, amide, or ester linkages. Y is preferably selected so that the dicarboxylic acids are either important naturally-occurring metabolites or highly biocompatible compounds. Preferred dicarboxylic acids therefore include the intermediate dicarboxylic acids of the cellular respiration pathway known as the Krebs Cycle. These dicarboxylic acids include α-ketoglutaric acid, succinic acid, fumaric acid, malic acid and oxaloacetic acid, for which Y is —CH2-CH2-C(=O)—, —CH2-CH2-, —CH=CH—, —CH2-CH(—OH)—, and —CH2-C(=O)—, respectively.

In particular embodiments, Y in Formula 3 is a straight chain alkylene group having 2-8 carbons.

In particular embodiments, Formula 3 is one of the following dicarboxylic acid, namely succinic acid, glutaric acid, diglycolic acid, adipic acid, 3-methyladipic acid, suberic acid, dioxaoctadioic acid and sebacic acid. Preferred dicarboxylic acids are succinic acid and adipic acid.

When polymerized, the tyrosine-derived monomers of Formula 2 and the dicarboxylic acids of Formula 3 give rise to polyarylates that can be represented by Formula 4.

Formula 4

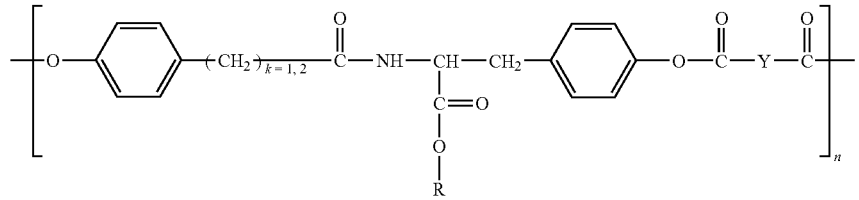

where R and Y are as described above. In this formula, as in other formulas herein, an "n" outside brackets or parentheses, and having no specified value, has its conventional role in the depiction of polymer structures. That is, n represents a large number, the exact number depending on the molecular weight of the polymer. This molecular weight will vary depending upon the conditions of formation of the polymer.

A preferred subset of the polyarylates of Formula 4 is the subset where k=2 and both R and Y are straight chain alkyl groups. This polyarylate subset can be represented by Formula 5.

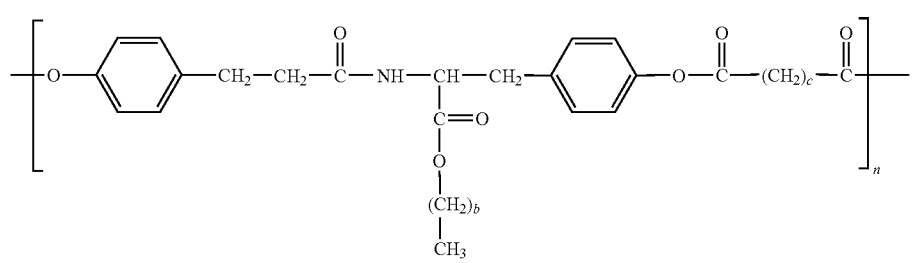

Formula 5

In Formula 5, b=1-17 and c=1-18. In preferred embodiments, b=1-7 and c=2-8. A preferred polyarylate for use in the present invention is the polyarylate of Formula 5 where b=1 and c=2. This polyarylate is referred to herein as p(DTE succinate). This name illustrates the nomenclature used herein, in which the names of polyarylates are based on the monomers making up the polyarylates. The "p" stands for polymer; the "DTE" stands for Desaminotyrosyl Tyrosine Ethyl ester; the "succinate" refers to the identity of the dicarboxylic acid. p(DTE succinate) is formed by the polymerization of the tyrosine-derived monomer desaminotyrosyl tyrosine ethyl ester and the dicarboxylic acid succinic acid.

Another preferred polyarylate for use in the present invention contains three monomer subunits: desaminotyrosyl tyrosine ethyl ester, succinic acid, and desaminotyrosyl tyrosine. The monomer desaminotyrosyl tyrosine (referred to herein as "DT") is the same as desaminotyrosyl tyrosine ethyl ester except that it contains a pendant free carboxylic acid group rather than the pendant ethyl ester of desaminotyrosyl tyrosine ethyl ester.

The inclusion of a certain percentage of desaminotyrosyl tyrosine monomers in the polymer produces a polyarylate with that certain percentage of free carboxylic acid groups in the pendant chains. The structure of the polyarylate corresponding to p(DTE succinate) but having free carboxylic acid groups in the pendant chains can be represented by Formula 1.

In Formula 1, or for any polymer having tyrosine-derived diphenol free acid moieties and tyrosine-derived diphenol ester moieties, a is a number between 0.01 and 0.99 that represents the mole fraction of tyrosine-derived monomer that is esterified, i.e., without a free carboxylic acid group. It is understood that the depiction of the tyrosine-derived monomers without and with free carboxylic acid groups as alternating in Formula 1 is for the sake of convenience only. Actually, the order in which tyrosine-derived monomers without free carboxylic acid groups and tyrosine-derived monomers with free carboxylic acid groups appear in the polyarylate generally will be random, although the overall ratio in which these two monomers appear will be governed by the value of a. Preferred values of a are: 0.97, 0.96, 0.95, 0.94, 0.93, 0.92, 0.91, 0.90, 0.89, 0.88, 0.87, 0.86, 0.85, 0.84, 0.83, 0.82, 0.81, and 0.80, 0.75, 0.70, 0.65, 0.60 and 0.55. Ranges for "a" also include 0.95-0.60, 0.90-0.70, and 0.95-0.75

The presence of free carboxylic acid groups and their percentage is indicated in the nomenclature used herein by modifying the name of the polyarylate in the manner illustrated for p(DTE succinate) as follows: p(5% DT, DTE succinate) indicates p(DTE succinate) with 5% free carboxylic acid groups, p(10% DT, DTE succinate) indicates p(DTE succinate) with 10% free carboxylic acid groups, p(15% DT, DTE succinate) indicates p(DTE succinate) with 15% free carboxylic acid groups, etc.

Formula 1

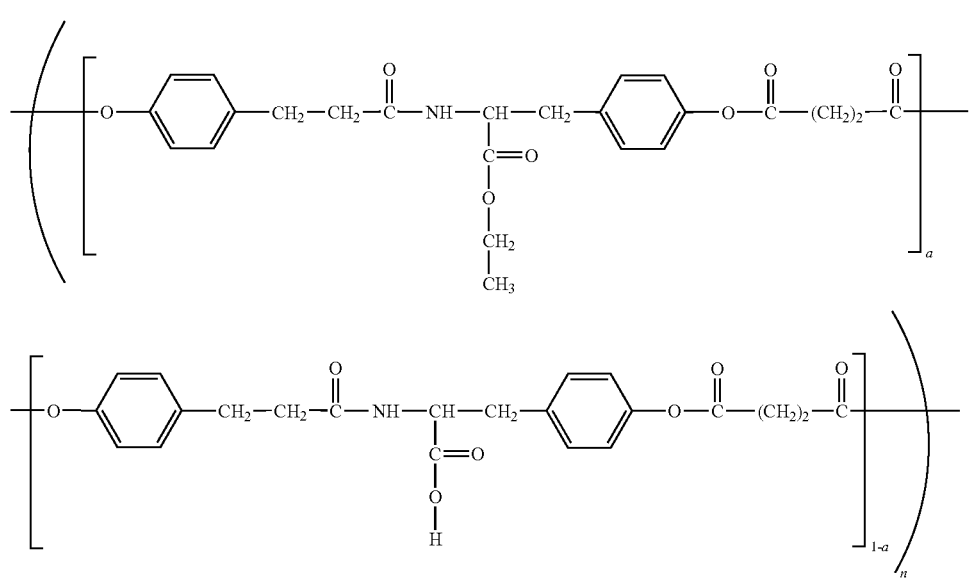

Another preferred polyarylate for use in the present invention is p(DTE adipate). p(DTE adipate) is formed by the polymerization of the tyrosine-derived monomer desaminotyrosyl tyrosine ethyl ester and adipic acid. Also preferred is p(DTE adipate) in which some of the pendant groups are free carboxylic acid groups, e.g., p(10% DT, DTE adipate), p(15% DT, DTE adipate), etc.

In general, any of the polyarylates employed in the present invention can contain any desired percentage of pendant groups having free carboxylic acid groups. Thus, the present invention includes compositions of matter in which an NSAID is embedded, dispersed, or dissolved in a polyarylate polymer matrix where the polyarylate polymer has the structure shown in Formulas 4 or 5 except that a certain percentage of the pendant chains are free carboxylic acid groups rather than esters. The structure of the polyarylate polymer similar to Formula 4, but having free carboxylic acid groups in the pendant chains is shown in Formula 6.

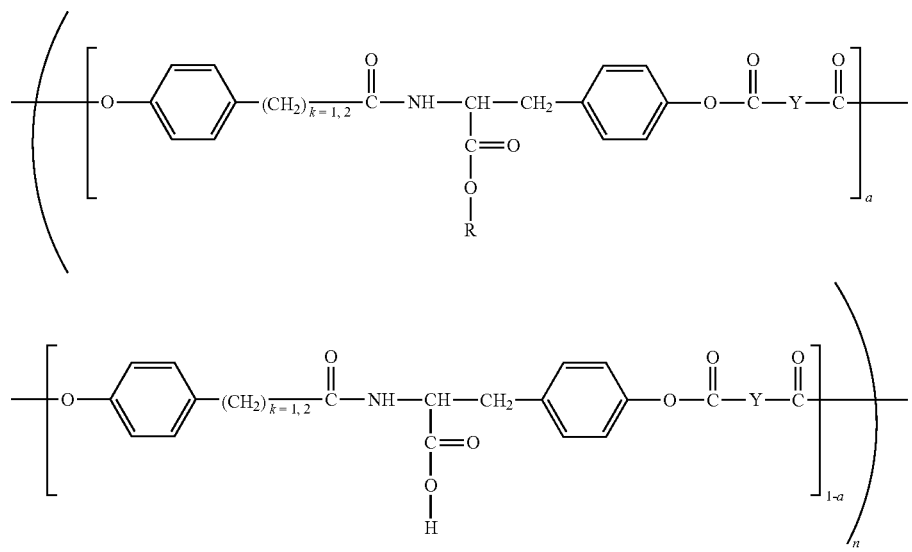

Formula 6

In Formula 6, R and Y are as in Formula 4. Usually, both instances of Y will be the same but this does not have to be the case a is as defined above for Formula 1.

The structure of the polyarylate polymer similar to Formula 5, but having free carboxylic acid groups in the pendant chains can be represented by Formula 7.

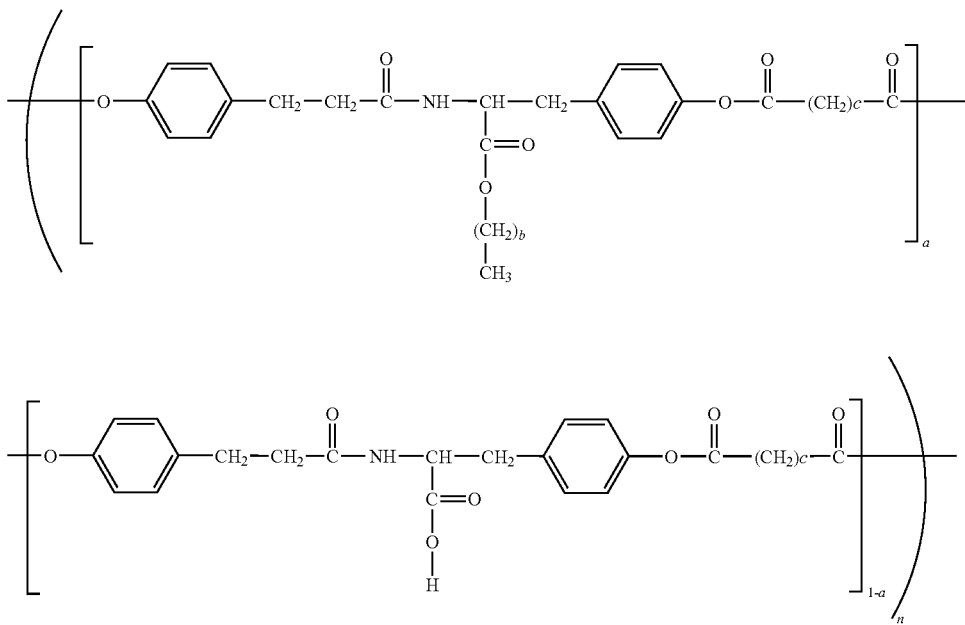

Formula 7

In Formula 7, b and c are as in Formula 5. Usually, both instances of c will be the same. Preferred values of b are 1, 5, and 7; preferred values of c are 2, 4, 6, and 8. a is as defined in Formula 1.

The incorporation of free carboxylic acid groups in the polyarylates has the effect of accelerating the rate of polymer degradation and resorption when the polyarylates are placed in physiological conditions, e.g., implanted into the body of a patient, as in a wound site. The presence of the free carboxylic acid groups also affects the behavior of the polyarylate in response to pH. Polyarylates having a relatively high concentration of pendent carboxylic acid groups are stable and water insoluble in acidic environments but dissolve or degrade rapidly when exposed to neutral or basic environments. By contrast, copolymers of low acid to ester ratios are more hydrophobic and will not degrade or resorb rapidly in either basic or acidic environments.

Such characteristics imparted by the carboxylic acid groups allow for the production of drug delivery devices comprising polyarylates and NSAIDs that are tailored to degrade or be resorbed at predetermined rates, and to deliver predetermined amounts of NSAID at predetermined rates, by choosing the proper percentage of carboxylic acid groups in the polyarylate. In particular embodiments, the percentage of pendant chains that are free carboxyl groups in the polyarylate polymers used in the present invention is about 1-99%, 5-95%, 10-80%, 15-75%, 20-50%, or 25-40%. In particular embodiments, the percentage of pendant chains that are free carboxyl groups is about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25%.

Further polymers that can be used in the present invention are co-polymers of the tyrosine-based polyarylates described above and poly(alkylene oxides). Such co-polymers are described, e.g., in U.S. Patent Ser. No. 60/375,846 and U.S. Pat. Nos. 5,658,995, and 6,120,491, the disclosures of which are incorporated by reference herein. These co-polymers are random block copolymers of a dicarboxylic acid with a tyrosine-derived diphenol and a poly(alkylene oxide), wherein an equimolar combined quantity of the diphenol and the poly(alkylene oxide) is reacted with the dicarboxylic acid in a molar ratio of the diphenol to the poly(alkylene oxide) between about 1:99 and about 99:1 to give a polymer having the following structure In preferred embodiments, R4 is ethylene; R5 is ethyl; R6 is ethylene or butylene; R7 is ethylene; and all substituents on the benzene rings in the polymer backbone are in the para position.

The poly(alkylene oxide) monomer used to produce the polymer shown in Formula 8 can be any commonly used alkylene oxide known in the art, and is preferably a poly (ethylene oxide), polypropylene oxide), or poly(tetramethylene oxide). Poly(alkylene oxide) blocks containing ethylene oxide, propylene oxide or tetramethylene oxide units in various combinations are also possible constituents within the context of the current invention.

The poly(alkylene oxide) is most preferably a poly(ethylene oxide) in which x of Formula 8 is between about 10 and about 500, or about 20 and about 200. In certain embodiments, poly(ethylene oxide) blocks with a molecular weight of about 1,000 to about 20,000 g/mol are used.

While many biodegradable tyrosine-derived polyarylates are specifically illustrated above, further such polymers for use in the invention are described in U.S. Pat. Nos. 5,099,060; 5,216,115; 5,317,077; 5,587,507; 5,658,995; 5,670,602; 6,048,521; 6,120,491; 6,319,492; 6,475,477; 6,602,497; 6,852,308; 7,056,493; RE37,160E; and RE37,795E; as well as those described in U.S. Patent Application Publication Nos. 2002/0151668; 2003/0138488; 2003/0216307; 2004/0254334; 2005/0165203; and those described in PCT Publication Nos. WO99/52962; WO 01/49249; WO 01/49311; WO03/091337.

The tyrosine-derived diphenol compounds used to produce the polyarylates suitable for use in the present invention can be produced by known methods such as those described in, e.g., U.S. Pat. No. 5,099,060 and U.S. Pat. No. 5,216,115, the disclosures of which are incorporated by reference herein. The production of desaminotyrosyl tyrosine ethyl ester, desaminotyrosyl tyrosine hexyl ester, and desaminotyrosyl tyrosine octyl ester can also be carried out by known methods, see, e.g., Pulapura & Kohn, 1992, Biopolymers 32:411-417 and Pulapura et al., 1990, Biomaterials 11:666-678.

The dicarboxylic acids are widely available from a variety of commercial sources. A tyrosine-derived diphenol monomer and a dicarboxylic acid may be reacted to form a polyarylate suitable for use in the present invention according to the methods disclosed in U.S. Pat. No. 5,216,115, the disclosures of which are incorporated by reference herein. Accord- Formula 8

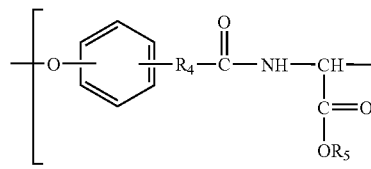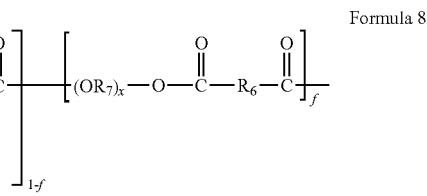

where $R_4$ is —CH=CH— or $(-CH_2-)_j$ in which j is between 0 and 8, inclusive; R5 is selected from the group consisting of straight and branched alkyl and alkylaryl groups containing up to 18 carbon atoms and optionally containing at least 1 ether linkage; R6 is selected from the group consisting of saturated and unsaturated, substituted and unsubstituted alkylene, arylene and alkylarylene groups containing up to 18 carbon atoms; each R7 is independently an alkylene group containing up to 4 carbon atoms; x is between about 5 and about 3,000; and f is the percent molar fraction of alkylene oxide in the copolymer and ranges between about 1 and about 99 mole percent.

ing to these methods, the diphenol compounds are reacted with the dicarboxylic acids in a carbodiimide-mediated direct polyesterification using 4-(dimethylamino)pyridinium-p-toluene sulfonate (DPTS) as a catalyst to form the polyarylates. Random block copolymers with poly(alkylene oxide) according to Formula 8 may be formed by substituting poly (alkylene oxide) for the tyrosine derived diphenol compound in an amount effective to provide the desired ratio of diphenol to poly(alkylene oxide) in the random block copolymer.

C-terminus protected alkyl and alkylaryl esters of tyrosine containing up to 8 carbon atoms can be prepared according to the procedure disclosed in J. P. Greenstein and M. Winitz, Chemistry of the Amino Acids, (John Wiley & Sons, New York 1961), p. 929. C-terminus protected alkyl and alkylaryl esters of tyrosine containing more than 8 carbon atoms can be prepared according to the procedure disclosed in U.S. Pat. No. 4,428,932.

N-terminus protected tyrosines can be prepared following standard procedures of peptide chemistry such as disclosed in Bodanszky, Practice of Peptide Synthesis (Springer-Verlag, N.Y., 1984).

The crude tyrosine derivatives are sometimes obtained as oils and can be purified by simple recrystallization. Crystallization of the pure product is accelerated by crystal seeding.

The diphenols can then be prepared by carbodiimide-mediated coupling reactions in the presence of hydroxybenzotriazide following standard procedures of peptide chemistry such as disclosed in Bodanszky, Practice of Peptide Synthesis (Springer-Verlag, N.Y., 1984) at page 145. The crude diphenols can be recrystallized twice, first from 50% acetic acid and water and then from a 20:20:1 ratio of ethyl acetate, hexane, and methanol, or, alternatively, by flash chromatography on silica gel, employing a 100:2 mixture of methylene chloride:methanol as the mobile phase. Desaminotyrosyl tyrosine esters also can be prepared by the carbodiimide mediated coupling of desaminotyrosine and tyrosine esters in the presence of hydroxybenzotriazole.

The diphenol compounds can then be reacted with dicarboxylic acids in a carbodiimide-mediated direct polyesterification using 4-(dimethylamino)pyridinium-p-toluene sulfonate (DPTS) as a catalyst to form polyarylates.

Because the diphenols of the present invention are base-sensitive, the polyarylates of the present invention are prepared by direct polyesterification, rather than by dicarboxylic acid chloride techniques. Polyesterification condensing agents and reaction conditions should be chosen that are compatible with the base-sensitive diphenol starting materials. Thus, the polyarylates can also be prepared by the process disclosed by Ogata et al., 1981, Polym. J., 13:989-991 and Yasuda et al., 1983, J. Polym. Sci: Polym. Chem. Ed., 21:2609-2616 using triphenylphosphine as the condensing agent; the process of Tanaka et al., 1982, Polym. J. 14:643-648 using picryl chloride as the condensing agent; or by the process of Higashi et al., 1986, J. Polym. Sci: Polym. Chem. Ed. 24:589-594 using phosphorus oxychloride as the condensing agent with lithium chloride monohydrate as a catalyst.

The polyarylates can also be prepared by the method disclosed by Higashi et al., 1983, J. Polym. Sci.: Polym. Chem. Ed. 21:3233-3239 using arylsulfonyl chloride as the condensing agent; by the process of Higashi et al., 1983, J. Polym. Sci.: Polym. Chem. Ed. 21:3241-3247 using diphenyl chlorophosphate as the condensing agent; by the process of Higashi et al., 1986, J. Polym. Sci.: Polym. Chem. Ed. 24:97-102 using thionyl chloride with pyridine as the condensing agent; or by the process of Elias, et al., 1981, Makromol. Chem. 182:681-686 using thionyl chloride with triethylamine. An additional polyesterification procedure is the method disclosed by Moore et al., 1990, Macromol. 23:65-70 utilizing carbodiimide coupling reagents as the condensing agents with the specially designed catalyst 4-(dimethylamino)pyridinium-p-tolune sulfonate (DPTS). A particular polyesterification technique modifies the method of Moore to utilize an excess of the carbodiimide coupling reagent. This produces aliphatic polyarylates having molecular weights greater than those obtained by Moore. When carbodiimides are used in peptide synthesis as disclosed by Bodanszky, Practice of Peptide Synthesis (Springer-Verlag, N.Y., 1984), between 0.5 to 1.0 molar equivalents of carbodiimide reagent is used for each mole of carboxylic acid group present. In the preferred methods disclosed herein, greater than 1.0 molar equivalents of carbodiimide per mole of carboxylic acid group present are used. This is what is meant by describing the reaction mixture as containing an excess of carbodimide.

Essentially any carbodiimide commonly used as a coupling reagent in peptide chemistry can be used as a condensing agent in the preferred polyesterification process. Such carbodiimides are well-known and disclosed in Bodanszky, Practice of Peptide Synthesis (Springer-Verlag, N.Y., 1984) and include dicyclohexylcarbodiimide, diisopropylcarbodiimide, 1-(3-dimethylaminopropyl)-3-ethyl carbodiimide hydrochloride, N-cyclohexyl-N'-(2'-morpholinoethyl)carbodiimide-metho-p-toluene sulfonate, N-benzyl-N'-3'-dimethylaminopropyl-carbodiimide hydrochloride, 1-ethyl-3-(3-dimethylaminopropyl)carbodiimide methiodide, N-ethylcarbodiimide hydrochloride, and the like. The preferred carbodiimides are dicyclohexyl carbodiimide and diisopropylcarbodiimide.

A reaction mixture is formed by contacting equimolar quantities of the diphenol and the dicarboxylic acid in a solvent for the diphenol and the dicarboxylic acid. Suitable solvents include methylene chloride, tetrahydrofuran, dimethylformamide, chloroform, carbon tetrachloride, and N-methyl pyrrolidinone. It is not necessary to bring all reagents into complete solution prior to initiating the polyesterification reaction, although the polymerization of slightly soluble monomers such as desaminotyrosyl tyrosine ethyl ester and succinic acid will yield higher molecular weight polymers when the amount of solvent is increased. The reaction mixture can also be heated gently to aid in the partial dissolution of the reactants.

The polymer molecular weight significantly increases as the amount of coupling reagent used is increased. The degree of molecular weight increase only begins to level off around four molar equivalents of carbodiimide per mole of carboxylic acid group. Increasing the amount of coupling reagent beyond four equivalents of carbodiimide has no further beneficial effect. While quantities of carbodiimide greater than four equivalents are not detrimental to the polyesterification reaction, such quantities are not cost-effective and are thus not favored for this reason.

Carbodiimide-mediated direct polyesterification can be performed in the presence of the catalyst 4-(dimethylamino) pyridinium-p-toluene sulfonate (DPTS). DPTS is prepared in accordance with the procedure of Moore et al., 1990, Macromol., 23:65-70. The amount of DPTS is not critical because the material is a true catalyst that is regenerated. The catalytically effective quantity is generally between about 0.1 and about 2.0 molar equivalents per mole of carboxylic acid group, and preferably about 0.5 equivalents per mole of carboxylic acid group.

The reaction proceeds at room temperature, or about 20-30° C. The reaction mixture can be heated slightly (<60° C.) prior to carbodiimide addition to partially solubilize less soluble monomers. However, the polymerization reaction itself should be conducted between 20° C. and 30° C. Within this temperature range, the reaction can be continued, with stirring, for at least 12 hours, and preferably for from one to four days. The polymer is recovered by quenching the reaction mixture in methanol, from which the polyarylate usually precipitates while the residual reagents remain in solution. The precipitate may be separated by mechanical separations such as filtration and purified by solvent washing.

In a preferred procedure, equimolar amounts of pure, dried tyrosine-derived diphenol and dicarboxylic acid are weighed and placed in a round-bottomed flask, pre-dried at 130° C. A suitable magnetic stir bar is placed into the flask. Then 0.4 equivalents of DPTS are added. The flask is fitted with a septum and flushed with nitrogen or argon to remove traces of moisture from the reaction mixture. Next, a quantity of HPLC grade methylene chloride is added via a syringe and the reaction mixture is stirred vigorously to suspend the reactants. The amount of methylene chloride used will depend upon the solubility of the diphenol, or the dicarboxylic acid, or both monomers. At this stage, the reaction mixture may be slightly heated to partially dissolve the monomers. While it is not essential that the monomers be completely dissolved, the quantity of solvent should be sufficient to dissolve the polymer as it forms and thus slowly bring the monomers into solution.

4.0 equivalents of diisopropylcarbodiimide are then added to the reaction mixture via a syringe. After about 10 minutes, the reaction mixture becomes clear, followed by the formation of a cloudy precipitate of diisopropylurea. After stirring between 20° C. and 30° C. for one to four days, the reaction is terminated by pouring the reaction mixture slowly and with vigorous stirring into ten volumes of methanol. The polymer precipitates while the residual reagents remain dissolved in methanol, resulting in the formation of the clear supernatant.

The polymeric product is retrieved by filtration and washed with large amounts of methanol to remove any impurities. If desired, the polymeric products can be further purified by dissolving in methylene chloride (10% or 20% w/w) and reprecipitating in methanol. The polymeric product is then dried to constant weight under high vacuum.

In order to make polyarylates having free carboxylic acid groups in the pendant chains, it is not sufficient to simply use the above-described polymerization processes and include monomers having free carboxylic acid groups. This is because the free carboxylic acid groups would cross-react with the carbodiimide coupling reagents used in the above-described processes. Instead, the method described in U.S. Pat. No. 6,120,491, the disclosures of which are incorporated by reference herein, can be employed. In this method, a polyarylate is synthesized, e.g., by the processes described above, with the inclusion of a monomer having a protecting group on the pendant chain that can be selectively removed after the polyarylate is synthesized. This protecting group must be capable of being removed without significant degradation of the polymer backbone and without removal of ester groups from pendant chains at those positions where it is desired that free carboxylic acid groups not be present in the final polymer.

A preferred method uses benzyl esters as the protecting group. Thus, if it is desired to have a polyarylate with a certain percentage of free carboxylic acid groups, then one would produce an intermediate step polyarylate with that percentage of monomers having benzyl esters in their pendant chains. The benzyl esters are selectively removed by palladium-catalyzed hydrogenolysis in N,N-dimethylformamide (DMF) or similar solvents such as N,N-dimethylacetamide (DMA) and N-methylpyrrolidone (NMP) to form pendent carboxylic acid groups. Pure DMF, DMA, or NMP is necessary as the reaction solvent. The reaction medium must be anhydrous and the solvents have to be dried to ensure complete removal of all benzyl ester groups in the hydrogenolysis reaction. Essentially any palladium-based hydrogenolysis catalyst is suitable but, in preferred methods, the palladium catalyst is palladium on barium sulfate. A level of palladium on barium sulfate between about 5% and about 10% by weight is preferred. Preferred methods also use 1,4-cyclohexadiene, a transfer hydrogenolysis reagent, in combination with hydrogen gas as a hydrogen source. The polymer starting material having pendent benzyl carboxylate groups can be dissolved in dimethylformamide at a solution concentration (w/v %) between about 5% and about 50%, and preferably between about 10% and about 20%. For further details, U.S. Pat. No. 6,120,491 can be consulted.

The co-polymers of tyrosine-based polyarylates and poly(alkylene oxides) depicted in Formula 19 can be prepared by methods described in U.S. Pat. No. 6,048,521 and U.S. Pat. No. 6,120,491, the disclosures of which are incorporated by reference herein.

Preferred polyarylates have weight-average molecular weights above about 40-50 kd. A preferred weight-average molecular weight range is about 40 kd to about 400 kd; more preferably about 25 kd to about 150 kd; even more preferably about 50-100 kd. Molecular weights can be calculated from gel permeation chromatography (GPC) relative to polystyrene standards without further correction. The molecular weight of the polyarylate polymer used in the present invention is a factor that the skilled artisan will consider when developing a polyarylate/NSAID combination for a particular use. In general, keeping all other factors constant, the higher the molecular weight of the polymer, the slower will be the release rate of the NSAID. See FIG. 3.

Systematic variations in polyarylate properties can be obtained by varying the nature of the pendant group attached to the C-terminus of the tyrosine-derived diphenol and the methylene groups in the dicarboxylic acid. One property that can be varied is the glass transition (Tg) temperature of the polyarylate polymer. This is exemplified by the approximately 1° C. increments in the glass transition temperature observed in the series of polyarylate polymers described in Brocchini et al., 1997, J. Amer. Chem. Soc. 119:4553-4554. In general, keeping all other factors constant, the higher the Tg of the polymer, the slower will be the release rate of the NSAID. Therefore, one can vary the Tg of the polyarylate polymers, and thus the release rate of the NSAID, by adjusting the identity of the dicarboxylic acid and the pendant chain ester groups.

The polydispersity index (PDI) of the polyarylates should be in the range of 1.5 to 4, preferably 1.8 to 3. Manipulating the polydispersity provides another way to adjust the release rate of the NSAID. As shown herein, higher molecular weight polymers release NSAID more slowly than lower molecular weight polymers. Thus, a batch of a particular polymer with an average molecular weight of 80 kd and a PDI of 1.5 should release NSAID more slowly than another batch of the same polymer with an average molecular of 80 kd but a PDI of 3, since the second batch is more polydisperse and thus has more lower molecular weight components than the first batch.

The tyrosine-derived diphenol monomers and corresponding tyrosine-derived polyarylates are biocompatible. The dicarboxylic acids generally are naturally occurring metabolites like adipic acid and succinic acid. Since the polyarylates contain an ester linkage in the backbone, they are biodegradable and their degradation products, tyrosine, desaminotyrosine, and the dicarboxylic acids, all have known toxicity profiles. The polyarylates produce significantly less acid during their degradation process than the PLGA family.

Several members of the polyarylates useful in the present invention were extensively tested in a variety of in vitro and in vivo assays and were found to exhibit excellent biocompatibility (Hooper et al., 1998, J. Biomed. Mat. Res. 41:443-454). In long-term in vivo studies, the present inventors have determined that the degradation products of the polyarylates appear to be innocuous to surrounding tissue and promote ingrowth. In addition, surrounding tissue does not appear to exhibit inflammation in response to the polyarylate degradation products. Implants in sheep, rabbits, dogs, and rats have demonstrated minimal tissue reaction and no local or systemic toxicity. When used as a carrier for demineralized bone, these polymers induce bone ingrowth and complete regeneration of new bone within 60 days.

Choice of NSAID

A wide variety of NSAIDs are suitable for use in the present invention. The choice of NSAID may depend on such factors as: condition to be treated, the compatibility of the chemical nature (e.g., solubility, hydrophobicity) of the NSAID with the chosen polyarylate, safety profile of the NSAID, efficacy of the NSAID, dose requirements of the NSAID, cost of the NSAID, etc. Suitable NSAIDs include:

aspirin
aspirin compounds (ANACIN®, BAYER®, BUFFERIN®)
celecoxib (CELEBREX®)
diclofenac (VOLTAREN®)
diflunisal (DOLOBID®)
etodolac (LODINE®, ULTRADOL®)
fenoprofen calcium (NALFON®)
flurbiprofen (ANSAID®)
ibuprofen (MOTRIN®, ADVIL®, RUFEN®)
indomethacin (INDOCIN®)
ketoprofen
ketorolac tromethamine (ACULAR®, TORADOL®)
meclofenamate sodium (MECLOMEN®)
meloxicam (MOBIC®)
nabumetone (RELAFEN®)
naproxen (NAPROSYN®, ALEVE®)
oxaprozin (DAYPRO®)
piroxicam (FELDENE®)
rofecoxib (VIOXX®)
sulindac (CLINORIL®)
tolmetin sodium (TOLECTIN®)
nonacetylated salicylates
salsalate (salicylsalicylic acid) (DISALCID®)
choline magnesium trisalicylate (TRILISATE®)
choline salicylate (ARTHROPAN®) and
valdecoxib (BEXTRA®).

An additional class of drugs suitable for use are the lipoxygenases (LOX) inhibitors, e.g., ZUBRIN®, sold by Schering-Plough for use in dogs.

When combined with the polyarylates disclosed herein to form a composition that can be formed into an implant suitable for use as a drug delivery device, it is often desirable that the NSAID show zero order release kinetics for at least two weeks. Another desirable characteristic is that the implant cause minimal, or no, gastrointestinal toxicity. It is also desirable that the implant containing the NSAID be resorbed in at least four months. Especially preferred implants are those that combine all these desirable characteristics.

A preferred embodiment of the present invention comprises ketoprofen combined with a polyarylate disclosed herein in the form of an implant for the local delivery of ketoprofen. Ketoprofen has the following chemical structure:

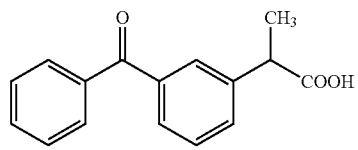 [SMILES: CC(C(=O)O)c1cccc(C(=O)c2ccccc2)c1]

The size of the implant needed to deliver a desired amount of NSAID by the methods of the present invention can be easily ascertained by those skilled in the art, taking into account such factors as: the condition to be treated, the identity of the NSAID to be delivered, the gender, age, general health, and size of the patient, and other factors that will be readily apparent. As a guide, the following two tables show how one skilled in the art might construct implants of the correct size to deliver some common NSAIDs at typical dosages.

Table 1 shows typical oral dosages of common NSAIDs.

TABLE 1

| NSAID | Dosage |
|---|---|
| Ibuprofen | 250 mg/4 times a day |
| Indomethacin | 25-50 mg/3 times a day |
| Ketoprofen | 100 mg/day |
| Piroxicam | 20 mg/day. |
| Rofecoxib | The recommended initial dose is 50 mg once daily. Subsequent doses should be 50 mg once daily as needed. |
| Celecoxib | 200 mg/day for arthritis |

TABLE 2 summarizes the dose requirements and the corresponding size of implants for a 2-week delivery system at the maximum oral dosage. The table assumes 50% loading of NSAID in the implant.

TABLE 2

| NSAID | Dose/day (mg) | Amount of drug needed (mg) | Size of implant (g) |
|---|---|---|---|
| Ibuprofen | 1,000 | 14,000 | 28 |
| Indomethacin | 150 | 2,100 | 4.2 |
| Ketoprofen | 100 | 1,400 | 2.8 |
| Piroxicam | 20 | 280 | 0.56 |
| Rofecoxib | 50 | 700 | 1.4 |
| Celecoxib | 200 | 2,800 | 5.6 |

Since the NSAID will be delivered locally by the implant, and the typical NSAID dosages are based on systemic administration, it is anticipated that the implant generally will be smaller than indicated and still produce good analgesia. The above tables are meant to serve as a guide to those skilled in the art rather than as a rule to be strictly followed. It will be apparent to those skilled in the art how to tailor the size of the implant to the purpose at hand.

NSAIDs are a very well studied class of pain relieving agents which work by inhibiting prostaglandin synthesis. NSAIDs are traditionally classified by their relative inhibitory effect on the COX-1 and COX-2 enzymes; however, many NSAIDs block both COX-1 and COX-2 and thus all have some potential side effects associated with cardiovascular events and gastrointestinal bleeding. An alternative mode of classifying NSAIDs is according to their chemical structure into propionic acid-based NSAIDs and acetic acid-based NSAIDs.

There is evidence that the structural differences between the acetic acid and propionic acid NSAID derivatives may have different effects on bone mineral density. For instance, clinical studies have indicated that propionic acid derivatives may have a greater protective effect on bone mineral density. Nonsteroidal anti-inflammatory drugs and bone mineral density in older women: The Rancho Bernardo study MORTON D. J. (1); BARRETT-CONNOR E. L. (1); SCHNEIDER D. L. (1); (1) University of California, San Diego, La Jolla, Calif., ETATS-UNIS. Journal of bone and mineral research 1998, vol. 13, no 12, pp. 1924-1931.

Therefore, dosage and amount of propionic acid versus acetic acid derivatives can be different and larger amounts of propionic acid derivatives may be more beneficial than acetic acid derivatives. Accordingly, propionic acid NSAID derivatives are useful for post-operative pain dosed over relatively long periods of time at high local concentrations. The use of only propionic acid derivatives and the dosing regimen are unique. Examples of propionic acid NSAID derivatives include, but are not limited to, ibuprofen, alminoprofen, dexibuprofen, dexketoprofen, fenbufen, fenoprofen, flunoxaprofen, flurbiprofen, ibuproxam, indoprofen, ketoprofen, ketorolac, loxoprofen, naproxen, oxaprozin, pirprofen, suprofen and tiaprofenic acid.

Examples of acetic acid NSAID derivatives include, but are not limited to, aspirin, the salicylates and diflunisal.

Compositions of Matter Comprising Polyarylates and NSAIDs

The present invention provides combinations of polyarylates and NSAIDs that are useful for the local, sustained delivery of NSAIDs. The combination can take the form of a mixture or dispersion of the NSAID in the polyarylate. The NSAID can be physically admixed, dispersed, or embedded in the polymer by methods known in the art such as, e.g., dissolving the polyarylate and NSAID together in an organic solvent and solvent casting a drug delivery implant from the common solution. Preferred organic solvents are chloroform, methylene chloride, tetrahydrofuran (THF), and ethyl formate/methanol. The polyarylate and the NSAID generally form a homogeneous solid polymer matrix where the NSAID is miscible in and evenly distributed throughout the polymer matrix.

In another method of making the polyarylate/NSAID combination, dry mixtures of polyarylate polymer and NSAID may be blended and then compression molded or extruded at an elevated temperature, e.g., 100-110° C., provided the NSAID is stable at those temperatures for the duration of manufacture. In another method of formulating the polyarylate/NSAID combination, dry mixtures of polyarylate polymer and NSAID are milled to form powders. The milled powders can be sieved to obtain powders of desired particle size. The size of the particles can be controlled in order to produce desired rates of release of the NSAID. In general, larger sized particles will lead to slower release rates than smaller sized particles. A preferred particle size is between about 50 to 100 microns.

A further method of making microparticles comprising a polyarylate and an NSAID comprises:
(a) preparing a first phase, the first phase comprising an organic solvent in which an NSAID and a polyarylate polymer are dissolved;
(b) preparing a second phase, wherein said second phase is an aqueous phase and the first phase is substantially immiscible in the second phase;
(c) combining the first phase and the second phase to form an emulsion in which said first phase is discontinuous and said second phase is continuous; and
(d) stirring the emulsion until the organic solvent in the first phase evaporates, wherein microparticles comprising the polyarylate and the NSAID are formed.

Mechanical agitation of the combined first and second phases or the addition of small drops of the first phase to the second phase can be used to form the emulsion. The temperature during the formation of the emulsion is not especially critical, but can influence the size and quality of the microparticles and the solubility of the NSAID in the second phase. It is desirable to have as little of the NSAID in the second phase as possible. It will be obvious to the skilled artisan that the temperature of the emulsion cannot be so high that the stability of the particular NSAID being incorporated in the microparticles is adversely affected. For most NSAIDs and polyarylates, the temperature can be from about 20° C. to about 60° C.

As a modification of the above process, rather than stirring the emulsion until the organic solvent in the first phase evaporates, a quench solution can be added to remove the organic solvent, thus forming microparticles.

The combination of polyarylate and NSAID can be worked up by known methods commonly employed in the field of synthetic polymers to produce a variety of useful articles with valuable physical and chemical properties that can be used as degradable biomaterials for medical implants to deliver local and/or sustained release of the NSAID. The useful articles can be shaped by conventional polymer-forming techniques such as extrusion, compression molding, injection molding, solvent casting, spin casting, and the like. Preferably, the implants are sterilized after or during their formation.

The present invention does not include combinations of polyarylates and NSAIDs where the NSAID is covalently bonded to a significant degree to a pendant carboxyl chain of the tyrosine-derived portion of the polyarylate.

A preferred form of implant comprising the polyarylate/NSAID compositions of the present invention is microspheres or microparticles, optionally suspended in a water-soluble paste, for direct application onto tissue or in an aqueous solution for injection. Thus, the present invention includes pharmaceutical compositions comprising microparticles, where the microparticles comprise a polyarylate polymer matrix in which an NSAID is mixed, dispersed, or embedded. Preferably, the microparticles are biodegradable and biocompatible and have a size range of from about 25 microns to about 750 microns.

Several procedures are available to prepare microspheres. The simplest is the single emulsion method. In this method, the polymer and drug are dissolved in an organic solvent that is immiscible with water. The organic solution of polymer and drug is added to an aqueous solution containing 1-2% polyvinyl alcohol (surfactant/stabilizer). The mixture is stirred and the solvent allowed to evaporate, leading to the formation of microspheres or microparticles containing the drug embedded in the polymer. The particles formed are collected by filtration or centrifugation, dried, and sieved to the desired size. This method works especially well when the drug to be incorporated has good solubility in the organic phase and limited solubility in the aqueous phase. Ketoprofen fits this profile. Particle size can be controlled by the concentration (viscosity) of polymer solution, stirring speed, concentration of polyvinyl alcohol, and rate of evaporation.

Accordingly, the present invention provides a method of making microspheres comprising a polymer matrix formed by a polyarylate polymer in which a non-steroidal anti-inflammatory drug (NSAID) is dispersed, dissolved, or embedded in the polyarylate polymer matrix where the method comprises:
(a) dissolving the polyarylate polymer and the NSAID in an organic solvent that is immiscible with water to form a polyarylate polymer/NSAID solution;
(b) adding the polyarylate polymer/NSAID solution to an aqueous solution of 1-2% polyvinyl alcohol to form a mixture;
(c) stirring the mixture until the organic solvent in the mixture evaporates;
thereby forming microspheres comprising a polymer matrix formed by a polyarylate polymer in which a non-steroidal anti-inflammatory drug (NSAID) is dispersed, dissolved, or embedded in the polyarylate polymer matrix.

The microsphere formulation may be stored dry as a powder in vials, suspended in a viscous, aqueous liquid or phosphate buffered saline (PBS), and injected through a 20-gauge or other needle at various sites proximal to a wound by a surgeon during or immediately after a surgical operation. The size of the needle required is not an important issue because the wound will already have been anesthetized, or the patient will be unconscious, in order to conduct the surgical operation. Thus the use of large microparticles is possible, if this proves advantageous.

The microspheres may also be formulated into a paste. To this end, the microspheres may be suspended in a polyethylene glycol (PEG)-based, water soluble gel that can be applied directly to the wound bed using a needleless syringe, or by other suitable means such as, e.g., a bandage. Other ointment bases can also be used to form pastes. Some suitable ointment bases include, but are not limited to, glycofurol, tetraglycol, tricaprilin, ethyl oleate, tristearin, triacetin, benzyl benzoate, glycerol, triethyl citrate, dibutyl sebacate, polyacrylic acid and PEG. An especially useful characteristic of certain combinations of polyarylates and NSAIDs of the present invention is that these combinations exhibit zero order release kinetics of the NSAID under physiological conditions. It appears that zero order kinetics can be achieved using a variety of polyarylates and NSAIDs, prepared in a variety of ways, e.g., by solvent casting, melt processing, etc., formed into a variety of shapes, e.g., films, microparticles, having a range of molecular weights, and stored under a variety of conditions. Zero order kinetics has even been observed under either sink or non-sink conditions. In preferred embodiments, zero order release kinetics occurs over a period of about 2 days to 60 days, preferably about 2 days to 30 days, and even more preferably about 7 days to 14 days. Zero order kinetics may be observed over the entire period of drug release. Alternatively, a short period of initial release may be observed followed by a longer period of release with zero order kinetics.

Utility

The polyarylate/NSAID combinations of the present invention can be formed into surgical implants for the treatment of various pain states, e.g., post-operative pain following surgery. The implants provide a continuous dose of NSAID analgesic for a prolonged period (e.g., up to 7 days or more) to an acute surgical wound. The implants will be useful to various surgical specialists (orthopedists, gynecologists, general and vascular surgeons, etc.) who may leave the implant in the superficial layers of the open surgical wound just before suturing it closed.

The implants of the present invention, comprising polyarylates and NSAIDs, provide local, sustained delivery of the NSAIDs. Consequently, the effective volume of distribution of the NSAID will be low (1% to 5% of the Vd associated with systemic distribution) because the drug delivery is specific to the surgical wound. Thus, a very small dose will achieve the same effect as that of a much larger systemic dose. "Leakage" of drug into the systemic circulation may eventually occur, although this is expected to be slow since the drug will be 99% bound to proteins immediately upon release (see, e.g., Physicians Desk Reference 1999: 3350-3353). Data presented herein show that an NSAID delivered by the methods of the present invention was effective at relieving pain at a wound site even while the systemic concentration of the NSAID was far below that which would have been therapeutically effective, had the NSAID been delivered systemically. Because of the low dose and the slow systemic release when the methods of the present invention are employed, effects upon the liver, kidneys, and gastrointestinal tract will be minimized.

Release of the NSAID from the compositions of the present invention can be primarily by a diffusional mechanism, primarily by degradation of the polyarylate polymer, or by a combination of both mechanisms. In a diffusional mechanism of drug release, the polyarylate remains mostly intact until essentially all of the NSAID is released from the polymer matrix. In a degradative mechanism of release, the NSAID is released from the polymer matrix as the polymer matrix erodes. By an appropriate selection of polymeric materials, a formulation can be made in which the resulting composition of polyarylate and NSAID exhibit either diffusional release or degradation release, or some mixture of the two types of release. This provides useful flexibility, allowing for the production of compositions that exhibit complicated, multiphasic release patterns, if such is desired.

When the compositions of the present invention are formulated as microparticles, even more flexibility is provided. The microparticles can be mixed by size or by type of polyarylate. Microparticles containing different NSAIDs can also be mixed. This variety can provide for the delivery of NSAID to the patient in a multiphasic manner and/or in a manner that provides different NSAIDs to the patient at different times, or a mixture of more than one NSAID at the same time. One can even include microparticles carrying non-NSAID agents. For example, antibiotics, vaccines, angiogenic agents, cytokines, or any desired active agent, can be provided to the patient.

The present invention can be used to overcome the problem of "burst" release that occurs soon after implantation of prior art devices for long term drug delivery. When burst release occurs, most of the drug leaches out of the drug delivery vehicle within the first 24 hours after implantation. The present invention provides drug delivery devices comprising a polyarylate matrix and an NSAID dispersed therein where the NSAID is released in a manner such that less than 50%, preferably less than 40%, more preferably less than 30%, and even more preferably less than 10-20% of the NSAID is released within the first 24 hours after implantation.

As used herein, "burst free release" provides that less than about 50% of the NSAID is released within 24 hours. To determine if burst free release has occurred, the release profile of the NSAID is measured in vitro in phosphate buffered saline at 37° C. The measurement can also be done in vitro under general physiological conditions 37° C. The in vitro determined release correlates with and is representative of effective burst-free, sustained released compositions with desirable in vivo efficacy for localized delivery.

As used herein, a "sustained release" formulation provides that release of the NSAID occurs for at least 2-3 days and for as long as 2-4 months, depending on the choice of NSAID, polymer, relative amounts of the NSAID and the polymer, and the physical form of the formulation (e.g., films, microparticles, microspheres, etc.). To determine if sustained release has occurred, the release profile of the NSAID is measured in vitro in phosphate buffered saline at 37° C. The measurement can also be done in vitro under general physiological conditions 37° C.

The present invention provides drug delivery devices comprising a polyarylate matrix and an NSAID dispersed therein where not more than about 1%, about 2%, about 3%, about 4%, about 5%, about 6%, about 7%, about 8%, or about 9% of the NSAID is released within the first 24 hours after implantation. The present invention provides drug delivery devices comprising a polyarylate matrix and an NSAID dispersed therein where not more than about 2%, about 3%, about 4%, about 5%, about 6%, about 7%, about 8%, about 9%, about 10%, about 11%, about 12%, about 13%, about 14%, about 15%, about 16%, about 17%, about 18%, or about 19% of the NSAID is released within the first 24 hours after implantation. In particular embodiments, the devices also provide zero order kinetics of NSAID release under physiological conditions. In particular embodiments, the zero order kinetics is provided for a period of time of about 2 days to 60 days, about 3 days to 50 days, about 4 days to 40 days, about 7 days to 30 days, about 10 days to 25 days, or about 14 days to 20 days. The period during which zero order kinetics occurs can be the period immediately following implantation, or it can a period that begins after a short period of initial release.

Even where complete relief of post-operative pain is not attained using the methods of the present invention, a reduction in opiate use can still be expected. Moreover, multi-drug analgesia (through use of the present invention as well as opiods) may be especially effective, since studies have demonstrated that such multi-drug analgesia is more effective than the pain relief associated with any single agent (Curatolo & Sveticic, 2002, Best Pract. Res. Clin. Anaesthesiol. 16:507-19).

The benefits of using the combination of polyarylates and NSAIDs of the present invention include:
Constant, rather than peak and trough, pain relief;
Stopping pain where it occurs—at the surgical site;
Eliminating or reducing the need for supplementary analgesia;
Not requiring the nauseated or sleepy patient to take pills or injections;
Avoiding the complications of narcotics;
Avoiding the complications of systemic NSAIDs;
Not requiring a skilled nurse to administer the analgesic;
No monitoring required; and
Cannot be abused as narcotics (overdosed, given to someone other than the patient).

The combination of polyarylates and NSAIDs of the present invention can be used in a variety of surgeries, including:
Inguinal and other hernia,
Carotid endarterectomy,
Coronary bypass,
Total hip replacement,
Hysterectomy,
Open thoracotomy,
Oral surgery, and
Orthopedic surgery, including knee, shoulder, ankle surgery, including arthroscopic surgery and open surgery Especially suitable surgeries for use of the present invention are:
Hernia repair,
Hysterectomy,
Plastic surgery, and
Dental surgery.

Another use for the present invention is to alleviate pain associated with cancer. Another use is to alleviate bone pain associated with osteomyelitis. A still further use is to provide a continuous, local, long-term source of NSAID to the brains of patients with Alzheimer's disease. Another use is to provide implants or injectables for insertion into an arthritic joint for the alleviation of pain and/or inflammation associated with arthritis. The present invention provides a biocompatible, hydrolytically degrading, drug delivery vehicle that provides more effective, less toxic dosing regimen for drugs used to prevent joint pain from surgery, osteoarthritis, or injury-induced joint pain. The present invention uses physiologically friendly, biomaterial-based formulations based on polyarylates that provide sustained release of drugs within the joint area, i.e., the intra-articular space. These formulations are injectable via syringe without the need for more invasive surgical procedures. The result is more effective, longer-term pain relief with lower side effects.

Site-specific delivery of drugs to the intra-articular space via the present invention provides a unique approach to the management of joint pain that meets a demanding set of conditions. The polyarylate-containing pharmaceutical compositions employed are resistant to the highly enzymatic and acidic environment found in the synovial fluid, biocompatible with cartilaginous and bony tissue, viscous, hydrophobic, and degrade into soft, water soluble components that will not harm the cartilage surface.

In one embodiment, the polyarylate polymer used for site-specific delivery to the intra-articular space has the structure

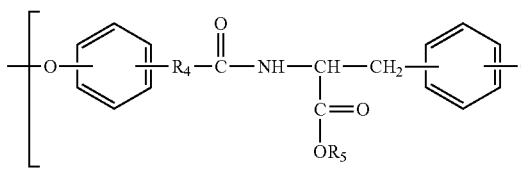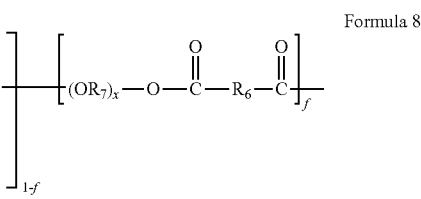

Formula 8 where R4 is —CH=CH— or (—CH2-)j in which j is between 0 and 8, inclusive; R5 is selected from the group consisting of straight and branched alkyl and alkylaryl groups containing up to 18 carbon atoms and optionally containing at least 1 ether linkage; R6 is selected from the group consisting of saturated and unsaturated, substituted and unsubstituted alkylene, arylene and alkylarylene groups containing up to 18 carbon atoms; each R7 is independently an alkylene group containing up to 4 carbon atoms; x is between about 5 and about 3,000; and f is the percent molar fraction of alkylene oxide in said copolymer and ranges between about 1 and about 99 mole percent;
or
the structure of Formula 8 where R4, R6, R7, x, and f are as described above and where a mole fraction of between 0.01 and 0.50 of R5 is hydrogen and the remaining mole fraction of R5 is as described above.

In one embodiment, the present invention includes pharmaceutical compositions useful for treating osteoarthritis comprising NSAIDs and the polyarylates described above where R7 is ethylene. Such polyarylates contain polyethylene glycol units (PEG) and are known as "PEG polyarylates." PEG is a widely employed lubricious unit that will reduce the glass transition temperature and hydrophobicity of the polyarylates. Methods of making polymers containing polyarylates and PEG are described herein. The resulting PEG polyarylates contain a series of highly biocompatible viscous liquids that can be injected via syringe into the intra-articular space. These PEG polyarylates, when combined with NSAIDs, function as drug delivery devices for the intra-articular space.

The present invention also provides a method of treating colorectal cancer using the polyarylate/NSAID combinations described herein. Colorectal cancer is generally treated by surgical resection of the involved area of the colon or rectum. A major problem following surgery is that the tumor tends to recur at or near the surgical site. By implanting a pharmaceutical composition comprising a polyarylate polymer in which an NSAID is dispersed, dissolved, or embedded in the polymer matrix at the or site (preferably during the same procedure in which the colon or rectum is resected), a means of local long term delivery of the NSAID can be achieved. Such long term release of NSAID at the site of highest danger for recurrence of the tumor is expected to have a protective effect in that the known ability of NSAIDs to retard angiogenesis of colorectal cancer cells (Li et al., 2002, Biochem. Biophys. Res. Comm. 299:886-890), would be expected to reduce the risk of or recurrence.

The combinations of NSAIDs and polyarylates of the present invention may be formed into microspheres or microparticles that are useful as an adjunct or replacement for commonly used oral or parenteral analgesics given post-operatively in the hospital and outpatient settings. The microspheres or microparticles, as well as other forms of the combination of NSAIDs and polyarylates of the present invention, provide several advantages when compared with traditional modes of post-operative pain relief:

- Continuous, rather than intermittent pain relief. The patient will not suffer the breakthrough pain associated with trough levels of analgesic experienced with intermittent oral or parenteral dosing. Further, potential toxicity that may occur during peak levels (especially when using opiates) will be avoided.
- No ingestion of pills or administration of injections. During the post-operative period many patients are nauseated, and the use of oral medications can be difficult and ineffective. Once the patient is discharged (which in the case of outpatient surgery may be only a few hours post-operatively) injection of analgesics is not generally feasible.
- Lessening of the need for opiates. Morphine, demerol, and related compounds have significant limitations in the treatment of post-operative pain. They depress central nervous system, respiratory, and gastrointestinal function and, of course, may be addicting. NSAIDs have been shown in many instances to be as effective as opiates in relieving surgical pain if given in sufficiently high dose.
- Site-specific treatment of pain and avoidance of systemic complications. Many patients cannot tolerate high doses of NSAIDs because of gastrointestinal, liver, and kidney toxicity. By positioning the NSAID at the site of injury and thromboxane synthesis, and allowing protein binding to hold it there, effective analgesia may be achieved with insignificant circulating levels of medication.
- There is no potential for abuse, overdosing or sharing of medications, in contrast to the situation in which a patient receives a prescription for oral opiates upon hospital discharge. [00133] The above advantages may be even more powerful in subsets of subjects for whom compliance is difficult, such as children and veterinary patients.

The present invention provides a method for site-specific drug delivery comprising implanting in the body of a patient in need thereof an implantable drug delivery device comprising a therapeutically effective amount of an NSAID in combination with one of the polyarylates described herein. The NSAID can be physically embedded, dispersed, or dissolved in the polyarylate polymer matrix and the polyarylate/NSAID combination shaped into the form of a suitable medical device. The drug delivery device can be any medical device which is suitable for the site-specific delivery of the NSAID. For example, suitable devices include shaped articles such as vascular grafts and stents, films, screws, rods, pins, bone plates, bandages, sutures, implantable sensors, barriers for surgical adhesion prevention, implantable drug delivery devices, porous scaffolds for tissue regeneration, and other therapeutic agent articles.

Alternatively, the polyarylate/NSAID combination of the present invention can be present as a coating on such devices, rather than making up the bulk of the device. For example, a paste formulation containing a polyarylate/NSAID composition of the present invention can be applied to a bandage that is then placed onto a wound, where the release of NSAID from the composition provides long term alleviation of pain and inflammation at the wound site. As another example, an implantable device, such as a pacemaker, defibrillator, neurostimulator, drug pum, catheter, a penile implant, etc., can be coated with one or more polymer/NSAID layers.

It will be appreciated by those skilled in the art that various omissions, additions and modifications may be made to the invention described above without departing from the scope of the invention, and all such modifications and changes are intended to fall within the scope of the invention, as defined by the appended claims. All references, patents, patent applications or other documents cited are herein incorporated by reference in their entirety.

The present invention may be better understood by reference to the following non-limiting Examples, which are provided only as exemplary of the invention. The following examples are presented to more fully illustrate the preferred embodiments of the invention. They should in no way be construed, however, as limiting the broader scope of the invention.

Example 1

Assays for Ketoprofen

The examples described herein employ the following methods for determining amounts and concentrations of ketoprofen.

Ketoprofen was obtained from SIGMA Chemical Company, St. Louis, Mo. (Cat #K 1751). USP grade ketoprofen was obtained from Spectrum Fine Chemicals, CA. Ketoprofen is readily soluble in alcohols, THF, Methylene chloride, acetone, DMSO, and acetonitrile. Its solubility in phosphate buffered saline (PBS) is 1 mg/ml.

The release medium for the ketoprofen release studies was PBS (0.1 M, pH 7.4) prepared by diluting PBS powder obtained from SIGMA (Cat #P3813) as per directions supplied.

HPLC Solvents

Acetonitrile (HPLC grade) was obtained from Fisher Scientific Company. Deionized water was collected from a BARNSTEAD Still. TFA was obtained from Acros Organics, a division of Fisher Scientific Company.

HPLC Assay for Ketoprofen

An HPLC method was developed for assaying ketoprofen. The column used for ketoprofen analysis was purchased from Perkin Elmer Corp., CT, with the following specifications—Brown Lee PECOSPHERE Silica C18, 3-micron particle size, 33×4.6 mm (Cat #0258-0164). The ketoprofen used for HPLC was from Sigma (Cat #K1751). Ketoprofen was assayed by UV at 215 nm. The HPLC system consisted of a Perkin-Elmer LC 410 pump with a UV LC 235 Array detector set at 215 nm and an ISS 200 auto sampler. Perkin-Elmer TurboChrom Workstation Version 6.1 software was used for data analysis. The HPLC method used is summarized in Table 3.

TABLE 3

| Step | Time, Minutes | % DI Water (TFA 0.1%) | % Acetonitrile (TFA 0.1%) | Flow Rate ml/min |
|---|---|---|---|---|
| 0 | 2 | 95 | 5 | 2 |
| 1 | 6 | 20 | 80 | 2 |
| 2 | 2 | 95 | 5 | 2 |

Under these conditions, ketoprofen elutes as a sharp peak with a retention time around 4.5 minutes.

Resolution of Ketoprofen from Polymer Degradation Products

The polymer degradation products for polyarylates containing both pendant ethyl esters as well as pendant free carboxyl groups are desaminotyrosyl tyrosine ethyl ester (DTE), desaminotyrosine (DT), desaminotyrosyl tyrosine (DAT), tyrosine ethyl ester (TE) and Tyr. DTE is resolved from Ketoprofen by the HPLC methods disclosed herein. DAT, TE and DT elute close to the injection peaks (0.3 minutes), well away from ketoprofen. If any peaks are seen around 0.4 minutes, the samples are reinjected using the following HPLC method (Table 4).

TABLE 4

HPLC Method used for identification of polymer degradation products

| Step | Time | % DI water (TFA 0.1%) | % Acetonitrle (TFA 0.1%) | Flow rate mL/min |
|---|---|---|---|---|
| 0 | 5 | 95 | 5 | 1 |
| 1 | 7.5 | 60 | 40 | 1 |
| 2 | 2.5 | 50 | 50 | 1 |
| 3 | 2 | 0 | 100 | 1 |
| 4 | 1 | 95 | 5 | 1 |

Calibration Curves

A calibration curve was constructed by sequential dilution of a 250 mg/25 ml (10 mg/ml) stock solution of ketoprofen in PBS. The concentration range was 0.4 mg/ml to 40 mg/ml. The curve was found to be linear in this range, with a correlation coefficient of 0.9918. An HPLC calibration curve was also prepared from weighed amounts of ketoprofen. This curve was identical to the curve obtained from sequential dilution of ketoprofen.

Reproducibility of Injection

The robustness of ketoprofen analysis was confirmed by checking the reproducibility of multiple injections. Four ketoprofen samples (1.7 mg, 2.2 mg, 2.8 mg or 4.1 mg, respectively) were prepared by carefully weighing out ketoprofen powder and dissolving it in PBS. The samples were injected 2 times in the HPLC. The retention times and area (UV*sec) were found to be reproducible with a variation of approximately 5%.

Detection Limit

The aim of this study was to determine the detection limits for ketoprofen in buffer using the HPLC system that is described above and that was used to quantify ketoprofen in the release studies described below. The detection limit is defined as the lowest concentration at which a peak for ketoprofen can be distinguished from baseline noise. 1.3 mg of ketoprofen was weighed into a vial and dissolved in 1 ml of buffer (PBS). This solution was then progressively diluted to give solutions with different amounts of ketoprofen. The concentrations of ketoprofen in the solutions were determined by HPLC using the method described above. The resulting data are summarized in Table 5. Based on these data, the limit of detection of ketoprofen is estimated to be about 0.01 µg/ml solution. The error in quantification at this concentration is >1,000%.

TABLE 5

Detection limits for ketoprofen

| Actual Amount in Solution, mg | Amount Calculated, mg | Error, % |
|---|---|---|
| 0.13 | 0.14 | 7.69% |
| 0.013 | 0.014 | 7.69% |
| 0.0013 | 0.0017 | 30.77% |
| 0.00013 | 0.00028 | 115.38% |
| 0.000013 | 0.0002 | >1,000 |

Quantification Limit

The quantification limit was determined by injecting sequentially diluted samples and estimating the amount of ketoprofen. The limit was defined as the concentration at which ketoprofen could be determined with an accuracy of ±2% after 3 repeated injections. This was determined to be about 50 µg/ml.

Determination of Loading
Method Development

Drug loading was estimated by an extraction procedure. 2 mg of the implant device was accurately weighed and dissolved in 1 ml of DMSO and precipitated out of 20 ml of PBS with vigorous shaking (on a Vortex mixer, for example). 1 ml of the suspension was filtered through a 0.45 µm TEFLON® filter. The filtered solution was then run through an HPLC system that was previously calibrated to estimate the amount of ketoprofen in the solution. This procedure was repeated three times for each device, each time sampling from a different portion of the device.

Determination of Loading
Solvent Free Process

The loading of ketoprofen in an implant device prepared by melt processing was determined using the above procedure. The theoretical loading was 20% and the average loading from six determinations was 16.1% (Std. dev., 0.9%). The lower average value is not unexpected because during the initial mixing step in the blender, the finer particles containing ketoprofen tend to fly around more than the larger polymer particles, leading to some loss of ketoprofen.

Example 2

Formulations for the Release Studies

Solvent Based Method 0.4 g of polyarylate polymer and 0.1 g of ketoprofen were weighed into a scintillation vial and dissolved in 5 ml of methylene chloride. The resulting solution was then filtered through a 0.45 µm TEFLON® filter (Gelman Sciences). After allowing the solution to settle for 5 minutes, it was poured onto a 5 cm diameter TEFLON® dish (Chemware Laboratory Products, N.J., USA). The solvent was allowed to evaporate slowly for a 24 hour period and then the film was vacuum dried at 50° C. for 24 hours. Three such devices were prepared for each release study. Other solvents that can be used are THF and a mixture of ethyl formate:methanol (80:20).

Solvent Free Process

A solvent free process approach was also developed. The polyarylate polymer and the drug were milled together in a mill/homogenizer for 1 minute. The resulting powder was compression molded at the following conditions: 110° C. throughout the molding cycle, 1 ton for 1 minute, 2 tons for 5 minutes and 3 tons for 5 minutes. This gave a uniform film with even loading of 20% at near 100% efficiency. Increasing the loading beyond 20% led to non-uniform films with uneven loading.

Preparation of Microparticles

Ketoprofen containing-polymer microparticles were prepared by grinding a preformulated film produced by solvent casting in a homogenizer M133/1281-0 (Biospec Products, OK) for different time periods and sieved through sieves of different sizes (>500 μm, 425-500 μm and 212-425 μm).

Example 3

Release Studies

Circular implant devices were punched from larger films using either a hand-held punch or a cork borer. The circular devices were then accurately weighed in a 20 ml scintillation vial and immersed into 20 ml of phosphate buffered saline, pH 7.4 (SIGMA Chemical Co., St. Louis, Mo., USA) (or in an appropriate container with sufficient buffer to maintain sink conditions, i.e., 10% of its maximum solubility at 100% release) and incubated at 37° C. 1 ml of the buffer was withdrawn periodically and run through the HPLC system described in Example 1. The amount withdrawn was replaced with an equal volume of fresh buffer. On average, three devices were used per study. Results are reported as a cumulative % released against time.

Study 1: Screening Study—Ketoprofen Release from a Variety of Polyarylates

The release of ketoprofen from different fast degrading polyarylates is shown in FIG. 1. Polyarylate polymers containing free acid pendant groups were used in this study so that the polymers would degrade and be resorbed in a relatively short time after ketoprofen release was complete. As shown in FIG. 1, the polyarylate polymers used were:

DTE co 10 DT Adipate=p(10% DT, DTE adipate), a polyarylate having 90% desaminotyrosyl tyrosine ethyl ester and 10% desaminotyrosyl tyrosine as the tyrosine-derived monomer, and having adipic acid as the dicarboxylic acid.

DTO co 20 DT Sebecate=p(20% DT, DTO sebecate), a polyarylate having 80% desaminotyrosyl tyrosine octyl ester and 20% desaminotyrosyl tyrosine as the tyrosine-derived monomer, and having sebacic acid as the dicarboxylic acid.

DTO co 10 DT Adipate=p(10% DT, DTO adipate), a polyarylate having 90% desaminotyrosyl tyrosine octyl ester and 10% desaminotyrosyl tyrosine as the tyrosine-derived monomer, and having adipic acid as the dicarboxylic acid.

The DTO-containing polymers could be formulated at lower temperatures than the DTE-containing polymer and could be formulated in solvents other than methylene chloride.

Some of the key findings from this study are:

The polymers with lower Tg (DTO polymers) release ketoprofen at a faster rate compared to the more hydrophilic, higher Tg polymer (DTE).

Ketoprofen release seems to be diffusion controlled for the DTO polymers (based on the shape of the release curve).

The release is fast and is complete within 4 to 5 days.

The chemistry of the backbone carboxylic acid (adipate vs. sebacate) has no effect on the rate of release of ketoprofen from these polymers.

Ketoprofen release from p(10% DT, DTE adipate) shows approximately zero order kinetics after an initial burst of 20%. Release extends for 2 weeks.

Study 2: Ketoprofen Release from P(10% DT, DTE Succinate) Films

Results from the previous study showed that the hydrophilic polymer p(10% DT, DTE adipate) had the ability to deliver ketoprofen in a linear fashion for 2 weeks. Also, the backbone dicarboxylic acid did not seem to influence the release kinetics to any great amount in the DTO series. It was decided to investigate whether p(10% DT, DTE succinate) would also show 2 week, zero order release kinetics. The DTE—succinate class of polymers are expected to degrade and resorb faster than the adipates, which would lead to a shorter ultimate resorption time, an advantage in certain applications.

Figure 2:
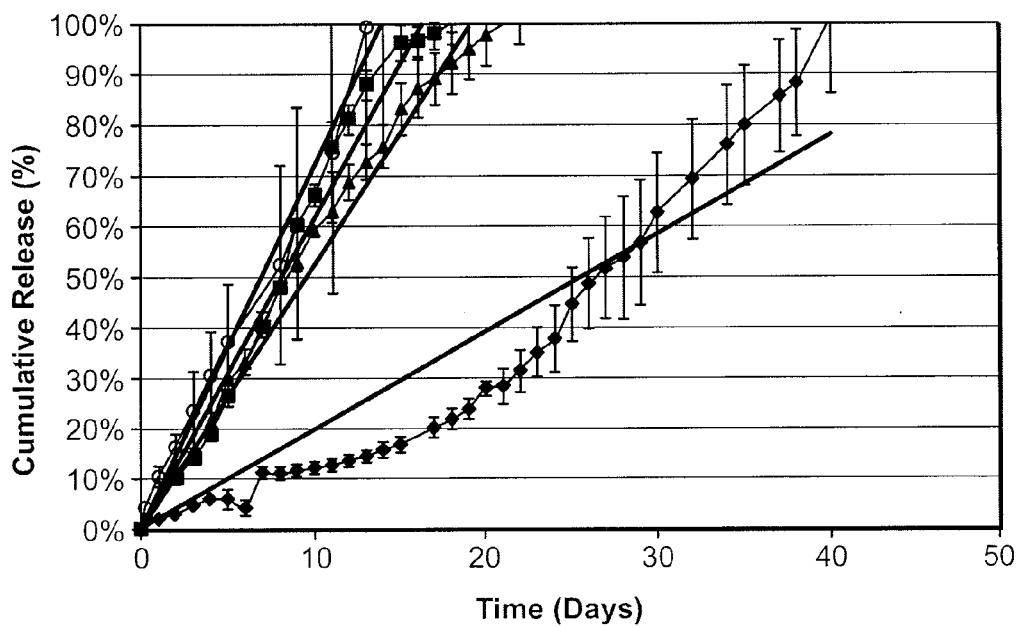
FIG. 2 shows the release of ketoprofen from p(10% DT, DTE succinate) at 4 different loadings: (♦) for 10%, (▲) for 20%, (■) for 30%, and (○) for 40%.

Solvent cast films were prepared from p(10% DT, DTE succinate) containing 4 different loadings of ketoprofen—10%, 20%, 30%, and 40% as described in Example 2. The films were clear and homogeneous based on visual inspection and digital scanning calorimetry (D SC) analysis. Small circular devices were punched out and the release study conducted as described previously. The release profiles are shown in FIG. 2 and show that ketoprofen release followed zero order kinetics at all four loadings.

The fastest release was obtained at the highest loading (40%), with about 8% ketoprofen being released per day. At 30% and 20% loadings, the amount released per day was 6% and 5%. At the lowest loading of 10%, about 2% of the ketoprofen was released per day.

The exact mechanism of release is not clear at this point. Since no additives or excipients were used in the films, the polymer appears to self-regulate the ketoprofen release, a phenomenon usually only associated with surface eroding polymers. However, p(10% DT, DTE succinate) does not appear to be a surface eroding polymer based on visual inspection. For example, physical handling of the devices did not show the thinning phenomenon associated with surface erosion. The mass loss of the polymer, which shows considerable molecular weight loss before resorption of the polymer, is consistent with a mechanism of bulk hydrolysis of the polymer rather than surface erosion.

Study 3: Effect of Polymer Molecular Weight on Release

Figure 3:
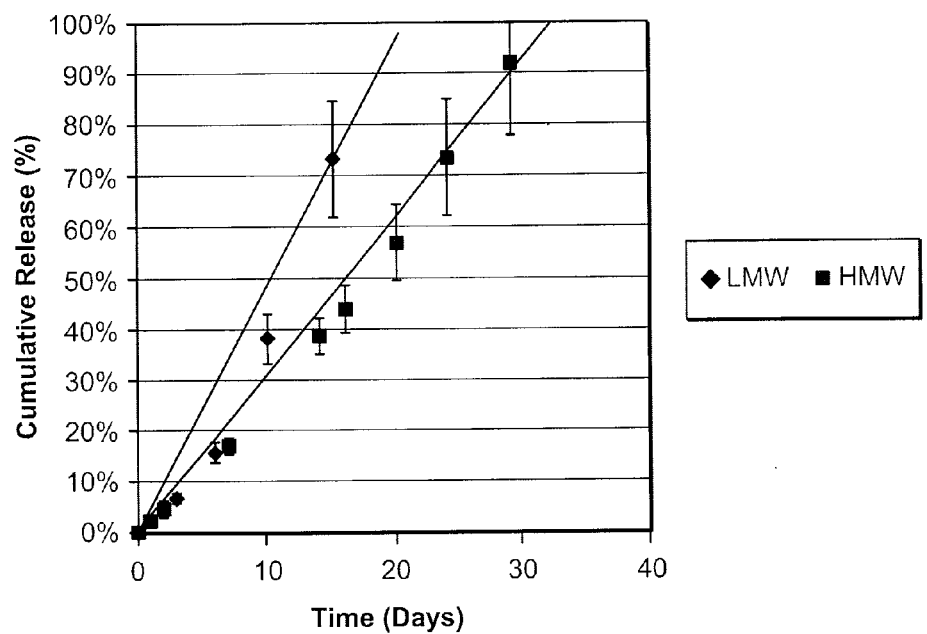
FIG. 3 shows the effect of molecular weight on ketoprofen release from p(10% DT, DTE succinate) with LMW (♦) and HMW (■).

The effect of starting molecular weight of the polymer on the ketoprofen release profile is shown in FIG. 3. Two p(10% DT, DTE succinate) polymers of different molecular weights 94,000 (high molecular weight, HMW) and 67,800 (low molecular weight, LMW) were used to prepare the films as described in Example 2. In this study, polymer molecular weight did not influence the zero order kinetics.

However, the ketoprofen release rate dropped for the HMW polymer from about 5% per day for the LMW polymer to about 3% per day for the HMW polymer, thus providing the means to alter and tailor release rates by varying the molecular weight of the polymer.

Study 4: Ketoprofen Release from Melt Processed, Compression Molded Film

To further avoid toxicities due to residual amounts of solvent, a melt process/compression molding method was developed to produce ketoprofen-containing devices employing p(10% DT, DTE succinate) as described in Example 2 (solvent free process section). Uniform films containing ketoprofen were obtained and release studies were also conducted as described in Example 2.

Figure 4:
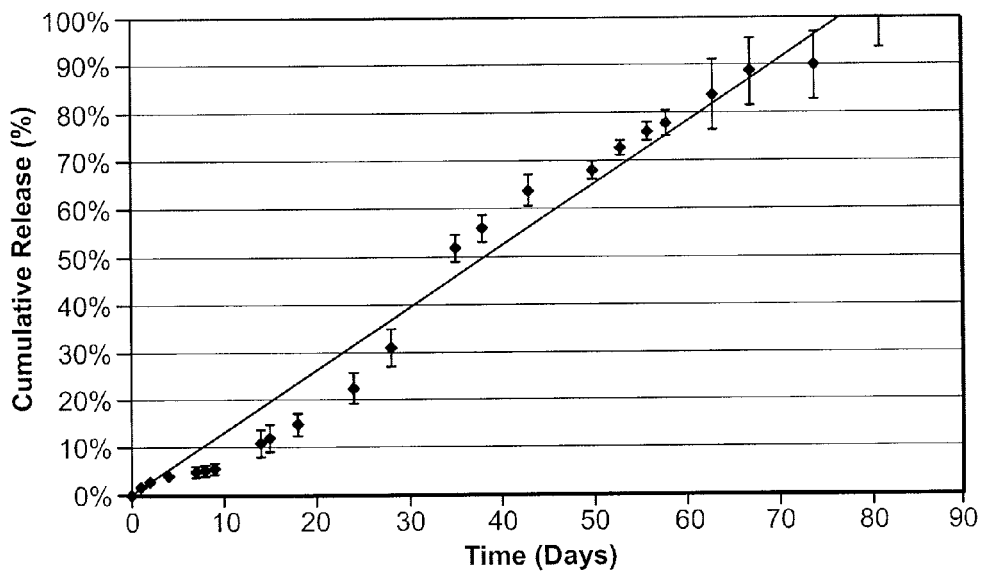
FIG. 4 shows the release of ketoprofen from p(10% DT, DTE succinate) melt processed/compression molded films.

The release profile in FIG. 4 demonstrates zero order kinetics. However, the rate of release was slower compared to solvent cast films—1.3% per day compared to 5% per day. Three factors appear to account for the difference: (1) density of the compression-molded devices, which are usually higher than those prepared by solvent casting; (2) trace amounts of solvent, which in solvent cast devices may plasticize the device, lower the Tg, and increase the release rate; and (3) device thickness is higher in the compression-molded devices, which reduces surface area and slows release.

Accordingly, melt processing and solvent casting affords another means to modulate the release rate of the NSAID to provide a device with a desired rate of release.

Study 5: Ketoprofen Release from Microparticles—Effect of Particle Size

To take advantage of the solvent free process and simultaneously increase the release rate, microparticles were made from compression molded films of study 4.

The microparticles were prepared by dry milling the film and sieving the particles as described in Example 2. Three particle size ranges were obtained 212 to 425 microns, 425-500 microns, and >500 microns.

Figure 5:
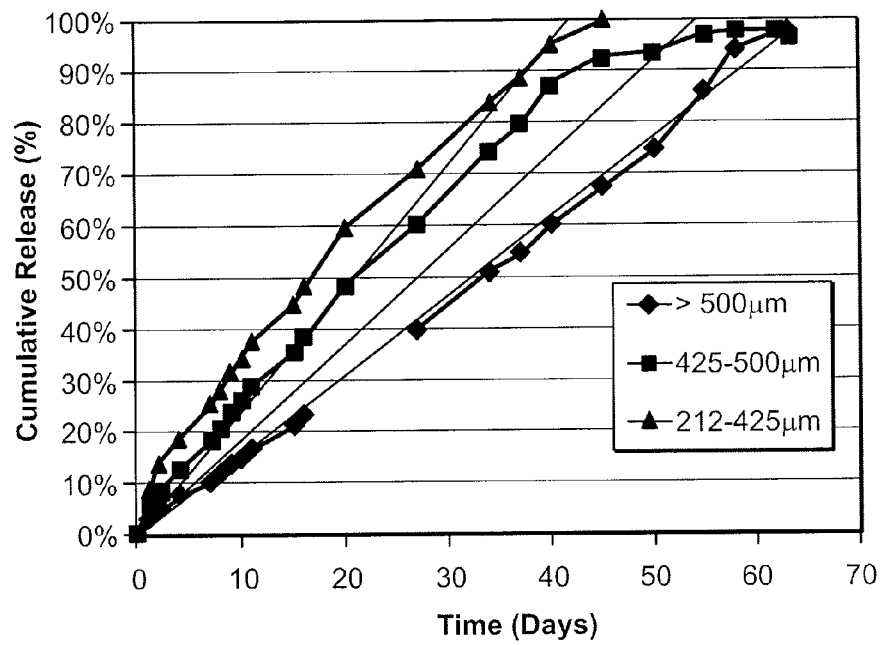
FIG. 5 shows the effect of particle size on the release of ketoprofen from melt processed/compression molded devices: (♦) for 212-425 μm particles, (■) for 425-500 μm particles and (♦) for >500 μm particles.

The results in FIG. 5 show that the smallest particles released ketoprofen at the fastest rate. Release was completed in about 40 days for the smallest particles and about 60 days for the largest. All sizes showed fairly linear release. The release rate in a similar range as that of the films used in the previous study. This approach provides a method to delifer ketoprofen in a sustained release fashion using a solvent free process.

Example 4

In Vivo Efficacy for Ketoprofen-Loaded Microparticles

This example demonstrates that a combination of the NSAID ketoprofen and the polyarylate p(10% DT, DTE succinate) has efficacy in vivo. A well-documented site-specific incisional pain model in rats was used to assess the effect of sustained release ketoprofen microparticles on incisional pain. The protocol was designed to assess three parameters: degree of relief of incisional pain from ketoprofen microparticles implanted at the wound site, concentration dependent effects, and the effect of the ketoprofen microparticles implanted distal to the wound site.

Polymer Characterization

Based on previous in vitro experiments, low molecular weight p(10% DT, DTE succinate) was used with 40% loading of ketoprofen. The p(10% DT, DTE succinate) polymer used for the ketoprofen in vivo release studies was characterized had a MW of 26 kDal and a Tg of 78.6° C.

Preparation of Ketoprofen-Loaded Polymer Microparticles

The p(10% DT, DTE succinate) was dried at 40° C. for 3 days and analyzed. 4.8 g of polymer was placed in a plastic beaker and topped with an excess of ethanol. The polymer was allowed to stand in ethanol at 50° C. for 2-3 hours. When the polymer became almost transparent, the ethanol was decanted and 3.2 g of ketoprofen was added. The ketoprofen was mixed with the polymer gel and placed in a vacuum oven while still wet. After overnight drying, the polymer/drug mixture was ground using a coffee grinder (overhead design). First, the polymer/drug mixture was cooled in liquid nitrogen. Then the polymer-drug mass was mixed with ground dry ice, added to the container of the grinder and ground at the highest speed for at least 5 min. The whole mixture of dry ice plus polymer/drug powder was transferred into a beaker, covered with Kimwipes™ and placed into a vacuum oven at 40° C. to dry overnight. The powder was then sieved using small plastic sieves resulting in ~1.8 g of 125-180 μm particles. Pure polymer powder for dilution purposes was prepared the same way but without ketoprofen.

The 40% ketoprofen-loaded microparticles were mixed with an approptiate amount of pure ground polymer to produce 20% and 5% ketoprofen-loaded microparticles. Samples were sterilized by ethylene oxide (ETO) treatment under conditions that left no detectable ETO.

In Vitro Release Study

Figure 6:
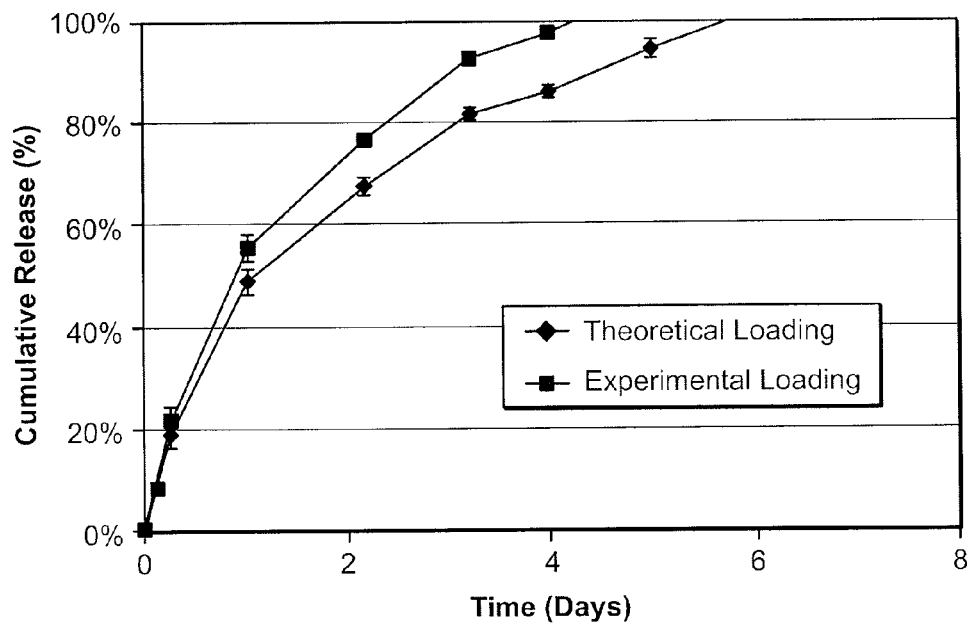
FIG. 6 shows in vitro ketoprofen release from microparticles used in the in vivo study described in Example 4: release for theoretical loading (♦) and release for actual loading (■).

The in vitro release profile of the microparticles was determined using dialysis tubes. The release profile for the ketoprofen-loaded microparticles (125-180 μm) is shown in FIG. 6. About 50% of the ketoprofen is released within 24 hours and 100% release is achieved after 6 days.

In Vivo Release Study

The ketoprofen-containing p(10% DT, DTE succinate) samples that were used in the in vivo pain study were as follows (1) control (no treatment); (2) polymer only; (3) 5% ketoprofen; (4) 20% ketoprofen (5) 40% ketoprofen; and (6) 40% ketoprofen, injected SC in neck.

Surgery

Rats (n=5) were anesthetized with 2% halothane delivered via a nose cone. The plantar aspect of the right hind paw was prepared in a sterile manner with a 10% povidone-iodine solution and draped. A 1 cm longitudinal incision was made with a number 11 blade through the skin and fascia of the plantar aspect of the paw, starting 0.5 cm from the proximal edge of the heel and extending toward the toes. The plants muscle was elevated and incised longitudinally; the muscle origin and insertion remained intact. After hemostasis with gentle pressure, the test compound was applied into the wound (groups 2-6). For closure, the skin was apposed with two mattress sutures of 5-0 nylon on an FS-2 needle. The rats were allowed to recover from anesthesia for 2 hours.

Pain Behavior

After recovery for 1-2 hours in clean bedding, the rats were placed on an elevated plastic mesh covered with a clear plastic cage top. Under these conditions, the animals will ambulate, explore, and eventually rest lying on the mesh. First, a cumulative pain score was used to evaluate the effect of the drug on non-evoked pain behavior. Unrestrained rats were placed on a smaller plastic mesh floor (grid 8×8 mm). Using an angled magnifying mirror, the incised and non-incised paws were viewed. Both paws of each animal were closely observed during a 1 min period repeated every 5 min for 1 hr. Depending on the position in which each paw was found during the majority of the 1 min scoring period, a 0, 1, or 2 was given. Full weight bearing of the paw (score=0) was present if the wound was blanched or distorted by the mesh. If the paw was completely off the mesh, a score of 2 was recorded. If the area of the wound touched the mesh without blanching or distorting, a 1 was given. The sum of the 12 scores (0-24) obtained during the one hr session for each paw. The difference between the scores from the incised paw and non-incised paw was the cumulative pain score for the one hr period.

Withdrawal threshold to punctate mechanical stimulation was determined using calibrated von Frey filaments applied from underneath the cage through openings (12×12 mm) in the plastic mesh floor to an area adjacent to the wound. Each von Frey filament was applied once starting with 15 mN and continuing until a withdrawal response occurred or 228 mN was reached. This was repeated a total of three times with a 5-10 min test-free period between withdrawal responses. The lowest force from the three tests producing a response was considered the withdrawal threshold. If there was no response to the 228 mN filament, the force of the next filament, 522 mN, was recorded.

Withdrawal latencies to heat were assessed by applying a focused radiant heat source on unrestrained rats. The heat stimulus was light from a 50 W projector lamp, with an aperture diameter of 6 mm, applied from underneath a heat-tempered glass floor (3 mm thick) on the middle of the incision. Paw withdrawal latencies were measured to the nearest 0.1 sec. Three trials 5-10 min apart were used to obtain an average paw withdrawal latency.

Behavioral testing was performed before incision, 2 and 4 hrs after incision, twice on postoperative day 1 and once on postoperative days 2, 3, 4, 6 and 8. Rats were euthanized after the 8th day of behavioral testing.

Results

Figure 7:
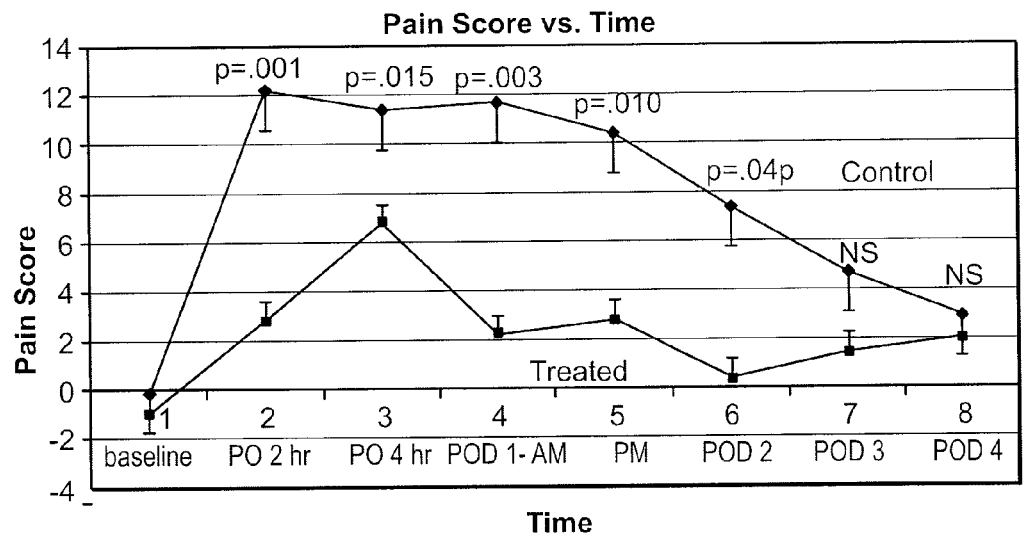
FIG. 7 shows pain scores over time for the combined treated groups (■, groups 3-5) and the combined non-treated groups (♦, groups 1 and 2).

FIG. 7 shows a statistically significant reduction in pain during the post-operative period. The upper trace shows the control results (combined groups 1 and 2, ♦) the lower trace shows the treated results (combined groups 3-5, ■). The times are PO2hr means two hours post-operation; POD 1-AM (PM), means one day post-operation with AM indicating in the morning and PM indicating in the afternoon, POD2 means 2 days post-operation, etc.

Figure 8:
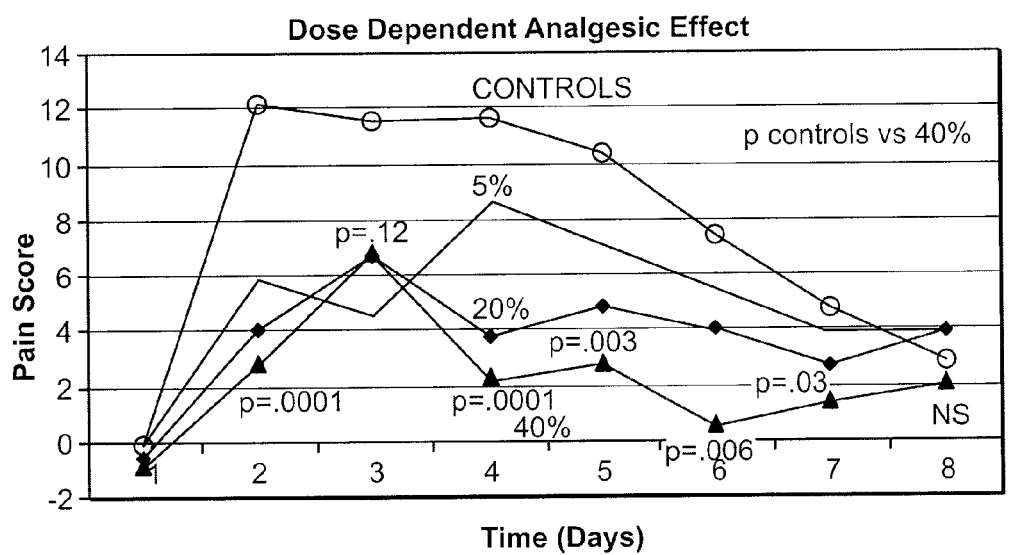
FIG. 8 demonstrates the in vivo dose-dependent analgesic effect for the combined treatment groups (3-5) for 40% (▲), 20% (♦), 5% (■) and control (○) loadings. The p values were calculated for the 40% loadings relative to combined controls on day 2 (p=0.0001) on day 3 (p=0.12) on day 4 (p=0.0001) on day 5 (p=0.003) on day 6 (p=0.006) and on day 7 (p=0.03). The differences on day 8 were not significant.

FIG. 8 demonstrates that the therapeutic effect was dose-dependent: the 40% ketoprofen-loaded polymer (▲) was more efficacious than the 20% (♦), which in turn was more effective than the 5% (■). The therapeutic effect of the 40% implant was statistically significant through the third post-operative day when compared with controls.

Figure 9:
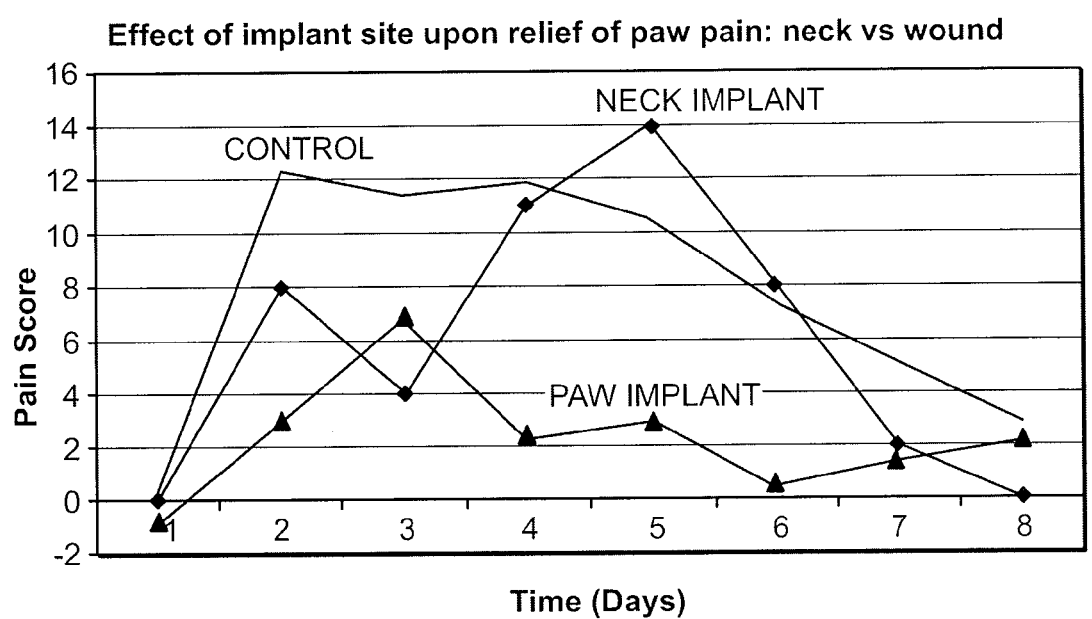
FIG. 9 shows pain scores over time for the combined non-treated control groups (■, groups 1 and 2), the 40% ketoprofen-loaded polyarylate injected into the neck (♦, 6), and the 40% ketoprofen-loaded polyarylate implanted into the paw (▲, 5).
Figures 10A, 10B, 10C, 10D:
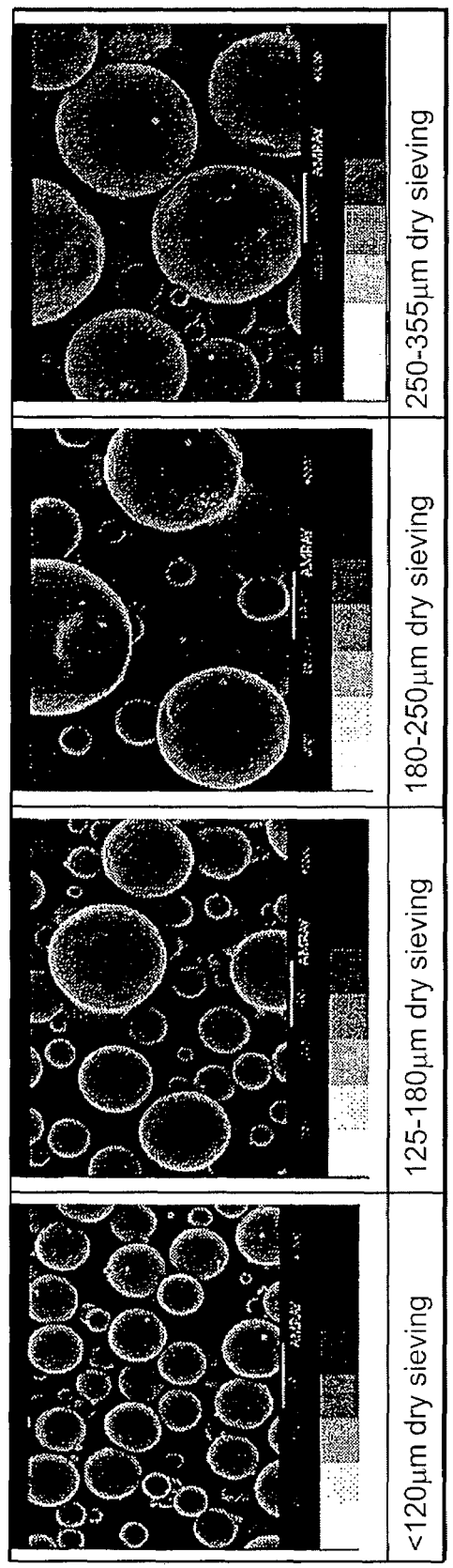
FIG. 10A: <125 μm.
FIG. 10B: 125-180 μm.
FIG. 10C: 180-250 μm.
FIG. 10D: 250-355 μm.

FIG. 9 shows that there was a site-specific effect: the 40% ketoprofen-loaded polymer injected into the neck (♦) did not give overall pain relief different from controls (■), while the 40% ketoprofen-loaded polymer in the paw (▲) was effective in relieving pain.

Ketoprofen Blood Levels

Blood was drawn from each animal on days 2 and 8 to determine serum ketoprofen levels. Although ketoprofen was detected on day 2, it was significantly below the effective serum concentration, indicating that ketoprofen acts via a local rather than a systemic mode of action. The ketoprofen blood levels are shown in Table 7.

TABLE 7

|  |  | 20% ketoprofen Incision | 40% ketoprofen Incision | 40% ketoprofen neck |
|---|---|---|---|---|
| Day 2 | Average (ng/mL) | 104.6 | 237.5 | 643.4 |
|  | SD | 38.3 | 158.9 | 215.2 |
| Day 8 | Average | 2.1 | 14.7 | 24.1 |
|  | SD | 4.6 | 14.0 | 9.1 |

On day 2, the highest amount of ketoprofen in blood came from the neck implant. The highest amount of ketoprofen released into serum via the wound site came from the 40% device, consistent with the pain scores. The data are consistent and in agreement with the in vitro data. The ketoprofen released from the 40% microparticles was about double the amount of ketoprofen released from the 20% microparticles (240 vs. 105). On day 8, the levels of ketoprofen had dropped to essentially zero for all devices.

Ketoprofen, when given orally for systemic distribution, is effective in the 1,000-4,000 ng/mL plasma concentration range. Table 7 indicates that during a time when the subjects experienced a significant analgesic effect (i.e., at Day 2), subtherapeutic levels of ketoprofen were circulating systemically.

Example 5

Preparation and Characterization of Ketoprofen Containing Microspheres p(15% DT, DTE Succinate), 40% Loading and 20% Loading 500 mg of polymer was dissolved in 5 ml of dichloromethane in a 20 ml scintillation vial to yield a clear solution. 100 mg (20% loading) or 333 mg (40% loading) ketoprofen was added to the solution and vortexed until the solution was clear. In a 250 ml beaker, 100 ml of a 2% polyvinyl alcohol (PVA) solution (pH 3, 1% acetic acid) was mixed with an overhead stirrer (2.5 cm crossed blades; 700-850 rpm). Stirring was stopped, the polymer/drug solution was added and stirring immediately resumed for at least one hour (until no smell of CH2Cl2 could be detected). The resulting microspheres (MSs) were filtered using a sintered glass funnel (coarse, 15 ml) and washed with 4×25 ml of nano pure water. Washed, wet MSs were frozen with liquid nitrogen and freeze dried for 24-48 h. Dry MSs were sieved using four different sized meshes (125, 180, 250, 355 μm) and the 125-180 μm portion was used.

p(10% DT, DTH Adipate), 20% and 40% Loading 500 mg of polymer was dissolved in 5 ml of ethyl acetate plus 0.25 ml of methanol in a 20 ml scintillation vial. The solution was not quite clear. 125 mg (20% loading) or 333 mg (40% loading) ketoprofen was added to the solution and vortexed until a clear solution was obtained. In a 250 ml beaker, 100 ml of a 2% PVA solution (pH 3, 1% acetic acid) and 5 ml ethyl acetate (to saturate the solution) was mixed using an overhead stirrer (2.5 cm crossed blades; 750 rpm). While stirring, the polymer/drug solution was carefully added and stirring continued for at least 2-4 hours. The resulting MSs were filtered using a sintered glass funnel (coarse, 15 ml) and washed in 4×25 ml of nano pure water. The washed, wet MSs were frozen with liquid nitrogen and freeze dried for 24-48 h. The dry MSs were sieved using four different sized meshes (125, 180, 250, 355 μm) and the 125-180 μm portion used.

Preparation of Large Batch of MSs Using p(15% DT, DTE Succinate) and 40% Ketoprofen (LB1)

5 g of polymer was dissolved in 50 ml of dichloromethane in a 100 ml flask using a magnetic stirrer, and filtered through a 1 μm glass or Teflon filter to produce a clear solution. 3.3 g (40% loading) of ketoprofen was added to the solution and stirred until a clear solution was obtained. In a 4 L beaker, 1,000 ml of a 2% PVA solution (pH 3, 1% acetic acid) was mixed using an overhead stirrer (7.5 cm crossed blades; 800 rpm). Stirring was stopped, the polymer/drug solution was added and stirring immediately resumed for at least two hours (until no smell of CH2Cl2 could be detected). The resulting MSs were filtered using a sintered glass funnel (coarse, 150 or 600 ml) and washed with 4×100 ml of nano pure water. The washed, wet MSs were frozen with liquid nitrogen and freeze dried for 24-48 h. The dry MSs were sieved using four different sized meshes (125, 180, 250, and 355 microns).

Loading Determination:

Loading was determined by dissolving a known weight of the ketoprofen-containing microspheres in a minimum amount of DMSO, extracting the ketoprofen into water, and determining the concentration of ketoprofen by HPLC. The average ketoprofen loading for LB1 was 37.7±2.0% for <125 μm microspheres; 38.7±0.8% for 125-180 μm microspheres; 40.4±1.0% for 180-250 μm microspheres loading; and 37.8±3.8% for 250-355 μm microspheres, all in reasonable agreement with the expected theoretical loading of 40%.

SEM Analysis

The various sieved fractions of LB1 microspheres were analyzed by SEM to evaluate size, shape and size distribution FIGS. 10A-D. A large number of smaller particles were attached to the larger particles, possibly due to static. Therefore, the particles were washed with water and sieved wet. The total yield of microspheres was 83%.

Preparation of Large Batch of Ketoprofen MSs from p(10% DT, DTE Succinate) (LB2)

5,000 mg of polymer was dissolved in 50 ml of dichloromethane in a 100 ml flask using a magnetic stirrer. 3,333 mg (40% loading) of ketoprofen was added to the solution and a clear solution obtained. In a 4 L beaker, 1,000 ml of a 1% polyvinyl alcohol (PVA) solution (pH 3, 1% acetic acid) was mixed using an overhead stirrer (7.5 cm crossed blades; 750 rpm). Stirring was stopped, the polymer/drug solution was added and stirring immediately resumed for at least two hours (until no smell of CH2Cl2 could be detected). The resulting MSs were sieved by washing through a set of sieves and a flat plastic funnel. At least 1 L of water was used.

Preparation of Ketoprofen-Containing MSs from p(10% DT, DTH Adipate) (LB3)

5,000 mg of polymer was dissolved in 50 ml of ethyl acetate plus 3 ml of methanol in a 100 ml flask using a magnetic stirrer. The polymer did not dissolve completely until the ketoprofen is added. 1,250 mg (17% loading) of ketoprofen was added and a clear solution obtained. In a 4 L beaker, 1,000 ml of a 1% polyvinyl alcohol (PVA) solution (pH 3, 1% acetic acid) was made from 200 ml 10% PVA, 10 ml acetic acid, 50 ml ethyl acetate and 740 ml pure water. The solution was mixed using an overhead stirrer (7.5 cm crossed blades; 700 rpm). The polymer/drug solution was filtered using a 1 μm glass filter, added to the PVA solution and stirring continued for at least two hours. The resulting MSs were sieved by washing (1045 mL water) through a set of sieves and a flat plastic funnel. Most of the resulting particles were small (<125 μm, but larger sizes were also obtained.

Preparation of Ketoprofen-Containing MSs from p(10% DT, DTE Succinate) in Large Scale LB4)

5,000 mg of polymer was dissolved in 50 ml of methylene chloride in a 100 ml flask using a magnetic stirrer. 3,333 mg (40% loading) of ketoprofen was added to the solution and a clear solution obtained. In a 4 L beaker, 1,000 ml of a 1% PVA solution (pH 3, 1% acetic acid), was prepared and mixed using an overhead stirrer (Teflon single blade—4.5"; 255 rpm). The polymer/drug solution was added to the PVA solution and stirring continued for at least two hours, until no methylene chloride could be smelled. The resulting MSs were sieved by washing through a set of sieves and a flat plastic funnel. All particles were smaller than 180 μm and most of them were smaller than 125 μm. Both fractions were freeze-dried.

Preparation of Ketoprofen-Containing MSs from p(10% DT, DTE Succinate) in Large Scale (LB5)

5,000 mg of polymer was dissolved in 50 ml of methylene chloride in a 100 ml flask using a magnetic stirrer. 3,333 mg (40% loading) of ketoprofen was added to the solution and a clear solution obtained. In a 4 L beaker, 1,000 ml of 1% PVA solution (pH 3, 1% acetic acid), was prepared and mixed using an overhead stirrer (Teflon single blade—4.5"; 150 rpm). The polymer/drug solution was added to the PVA solution and stirring continued for at least two hours, until no methylene chloride could be smelled. The resulting MSs were sieved by washing through a set of sieves and a flat plastic funnel. All particles were freeze-dried.

Preparation of Ketoprofen-Containing MSs from p(15% DT, DTE Succinate) in Large Scale (LB6)

5,000 mg of polymer was dissolved in 50 ml of methylene chloride in a 100 ml flask using a magnetic stirrer. 3,333 mg (40% loading) of ketoprofen was added to the solution and a clear solution obtained. In a 4 L beaker, 1,000 ml of 1% PVA solution (pH 3, 1% acetic acid), was prepared and mixed using an overhead stirrer (Teflon single blade—4.5"; 150 rpm). The polymer/drug solution was filtered through a 1 μm glass filter into the PVA solution and stirring continued for at least two hours (until no methylene chloride could be smelled). The resulting MSs were isolated by washing through a set of sieves and filtered using a flat plastic funnel. The wet MSs were freeze dried.

Preparation of Ketoprofen-Containing MSs from p(5% DT, DTE Succinate) in Large Scale (LB7)

5,000 mg of polymer was dissolved in 50 ml of methylene chloride in a 100 ml flask using a magnetic stirrer. 3,333 mg (40% loading) of ketoprofen was added to the solution and a clear solution obtained. In a 4 L beaker, 1,000 ml of a 1% PVA solution (pH 3, 1% acetic acid), was prepared from 200 ml 10% PVA, 10 ml acetic acid and 790 ml pure water by mixing with an overhead stirrer (Teflon single blade—4.5"; 150 rpm). The polymer/drug solution was added to the PVA solution and stirring continued for at least two hours, until no methylene chloride could be smelled. The resulting MSs were isolated by washing through a set of sieves and filtered using a flat plastic funnel. All MS particles were freeze-dried still wet. Table 8 summarizes conditions used for different MS scale-up batches.

TABLE 8

| Batch | Polymer, MW | Amount, mg | KP, mg | solvent, ml | PVA conc, % | Speed, rpm |
|---|---|---|---|---|---|---|
| LB1 | p (15% DT-DTE succinate) 61 kDa | 5000 | 3333 | 50 ml CH$_2$Cl$_2$ | 2 | 800 |
| LB2 | p (10% DT-DTE succinate) 25 kDa | 5000 | 3333 | 50 ml CH$_2$Cl$_2$ | 1 | 750 |
| LB3 | p (10% DT-DTH adipate) 79 kDa | 5000 | 1250 | 50 ml EtAc + 3 ml MeOH | 2 | 700 |
| LB4 | p (10% DT-DTE succinate) 88 kDa | 5000 | 3333 | 50 ml CH$_2$Cl$_2$ | 2 | 255 |

TABLE 8-continued

| Batch | Polymer, MW | Amount, mg | KP, mg | solvent, ml | PVA conc, % | Speed, rpm |
|---|---|---|---|---|---|---|
| LB5 | p (10% DT-DTE succinate) 85 kDa | 5000 | 3333 | 50 ml $CH_2Cl_2$ | 2 | 150 |
| LB6 | p (15% DT-DTE succinate)) 61 kDa | 5000 | 3333 | 50 ml $CH_2Cl_2$ | 2 | 150 |
| LB7 | p (5% DT-DTE succinate) 72 kDa | 5000 | 3333 | 50 ml $CH_2Cl_2$ | 2 | 150 |

Figure 11:
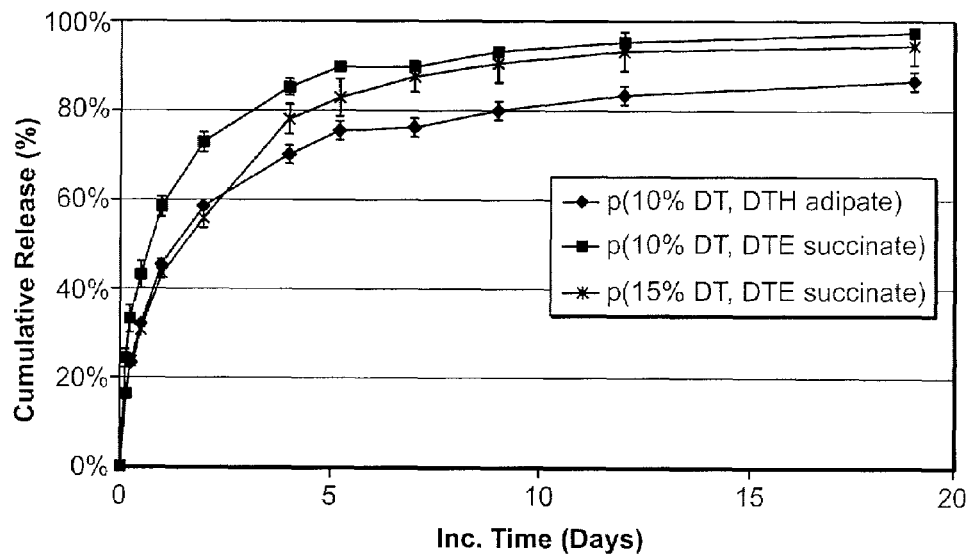
FIG. 11 shows the release ketoprofen rate from microspheres loaded with 40% ketoprofen in p(15% DT, DTE succinate), (*); with 40% ketoprofen in p(10% DT, DTE succinate), (■); or with 20% ketoprofen in p(10% DT, DTh adipate), (♦).

Cumulative release data was obtained for 19 days (FIG. 11) for MSs from: p(15% DT, DTE succinate) (LB 1w) washed 40% theoretical loading, 35.3%±1.6% average actual loading; p(10% DT, DTE succinate) (LB2), 40% theoretical loading, 39.6%±1.7% average actual loading; and p(10% DT, DTH adipate) (small batch preparation), 20% theoretical loading, 14.0%±1.2% average actual loading.

Example 6

Paste Formulations 180 mg of ketoprofen containing-microparticles produced as described in Example 4 were mixed with 540 mg of ointment base to form a paste. The ointment base compositions used in the study are given in Table 9 and resulted in pastes that were 25% microparticles and 75% ointment base.

TABLE 9

| | Compound 1 | Amount | Compound 2 | Amount | Temp. | Observations |
|---|---|---|---|---|---|---|
| 1 | PEG-400 | 60% | PEG-3350 | 40% | Heating gun | Sticky opaque mass |
| 2 | PEG-3350 | 40% | Dibutyl Sebacate | 60% | Heating gun | When hot-emulsion, cold-phase separation |
| 3 | PEG-3350 | 40% | Tricaprylin | 60% | Heating gun | When hot-emulsion, cold-phase separation |
| 4 | PEG-3350 | 40% | Ethyl Oleate | 60% | Heating gun | When hot-emulsion, cold-phase separation |
| 5 | PEG-8000 | 40% | Ethyl Oleate | 60% | Heating gun | When hot-emulsion, cold-phase separation |
| 6 | Tristearin | 40% | Ethyl Oleate | 60% | No heating needed | Suspension, but not water soluble |
| 7 | PEG-3350 | 40% | Tetraglycol | 60% | Heating gun | Goopy mass when cools down |
| 8 | Polyacrylic Acid 450K | 5% | Glycerol | 95% | Heating gun, High T | Foams, then sticky, transparent mass |

Compositions 1, 7, and 8 were selected for release studies. Table 10 provides further characteristics of those compositions.

TABLE 10

| Microparticle, μm | MW, kDal | Ointment base used | Expected loading | Final loading |
|---|---|---|---|---|
| Microparticles | 6 | none | 40% | 50.6(0.2)% |
| Sample 1 | 25 | (PEG400-60%, PEG3350-40%)-75% | 9% | 15.4(0.3)% |
| Sample 7 | 62 | (Tetraglycol-60%, PEG3350-40%)-75% | 11% | 13.2(0.1)% |
| Sample 8 | 25 | (Glycol-95%, p(Acrylic Acid)450,000-5%) - 75% | 9% | 17.9(0.9) |

Figure 12:
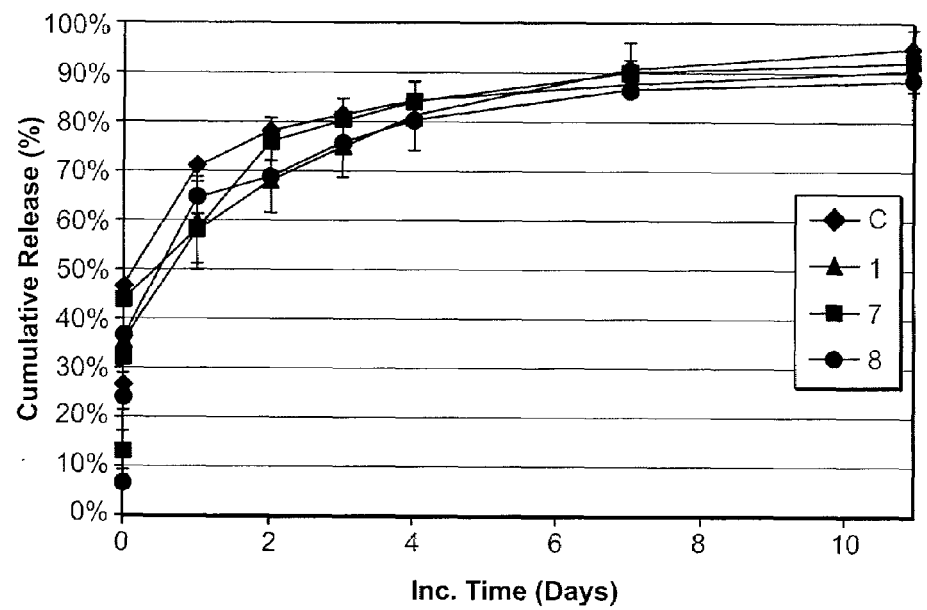
FIG. 12 shows the release rate of ketoprofen-containing microparticles formulated into apaste: (♦) control, (▲) sample 1, (*) sample 7, and (●) sample 8.

Between 10 to 25 mg of the paste containing microparticles were transferred to 50 ml polypropylene centrifuge tubes and 20 ml of PBS (pH 7.4, 0.01 M) was added. The tubes were capped and placed in a 37° C. incubator shaker and shaken at 200 rpm. At periodic intervals, 10 ml of buffer was pipetted out and 10 ml of fresh buffer was added. The samples were analyzed for ketoprofen using a standardized HPLC method. The release rate is shown in FIG. 12, as a plot of % cumulative release versus time. Pure microparticles were used as a control. The results demonstrate that release is not adversely affected by formulation into a paste.

Example 7

Additional Paste Preparations

To investigate the possibility of using three different paste compositions that are listed in USP as ointment bases in formulating a microsphere paste. The three bases are referred to as PEG ointment, Hydrophilic ointment, and Hydrophobic Ointment.

PEG Ointment

PEG 400 (600 g) was heated to 80° C. on a heating plate in a 1 L beaker. 400 g of PEG 3350 was added and the mixture stirred until the solid melted and a uniform melt was obtained. Heating was stopped. The hot viscous oil was poured into a 1 L glass jar and allowed to cool to room temperature, when it formed an opaque, soft gel.

Hydrophobic Ointment

White petrolatum (950 g) was heated to 80° C. on a heating plate in a 1 L beaker. White Wax (50 g) was added and the mixture stirred until the solid melted and a uniform melt was obtained. Heating was stopped. The hot viscous oil was poured into a 1 L glass jar and allowed to cool to room temperature when it formed an opaque soft gel.

Hydrophilic Ointment

White petrolatum (950 g) was heated to 80° C. on a heating plate in a 1 L beaker. All the other ingredients (except water) were added and the mixture stirred until the solid melted and a uniform melt was obtained. Water was then added and the mixture stirred until a homogeneous melt was obtained. Heating was stopped. The hot viscous oil was poured into a 1 L glass jar and allowed to cool to room temperature when it formed an opaque soft gel.

The final composition of the hydrophilic ointment was

| | |
|---|---|
| Methyl Paraben | 0.025% |
| Propyl Paraben | 0.015% |
| Sodium Lauryl Sulfate | 1% |
| Propylene Glycol | 12% |
| Stearyl Alcohol | 25% |
| White Petrolatum | 25% |
| Water | 37% |

Microsphere and Paste Preparations

Microspheres were prepared from p(5% DT, DTE succinate), p(10% DT, DTE succinate), and p(15% DT, DTE succinate) as described for LB5 (Example 5). The resulting microspheres were isolated by washing through set of sieves (125, 180, and 250 microns) and collected into 20 ml scintillation vials. The wet microspheres with some water were used for freeze drying. The microspheres were freeze dried for 48 hours. Recovery was 2.5 to 3.5 g of microspheres (110 to 180 microns).

Paste preparations were made by mixing the microspheres and the pastes in the ratio 25:75.

Release Study

Figure 13A:
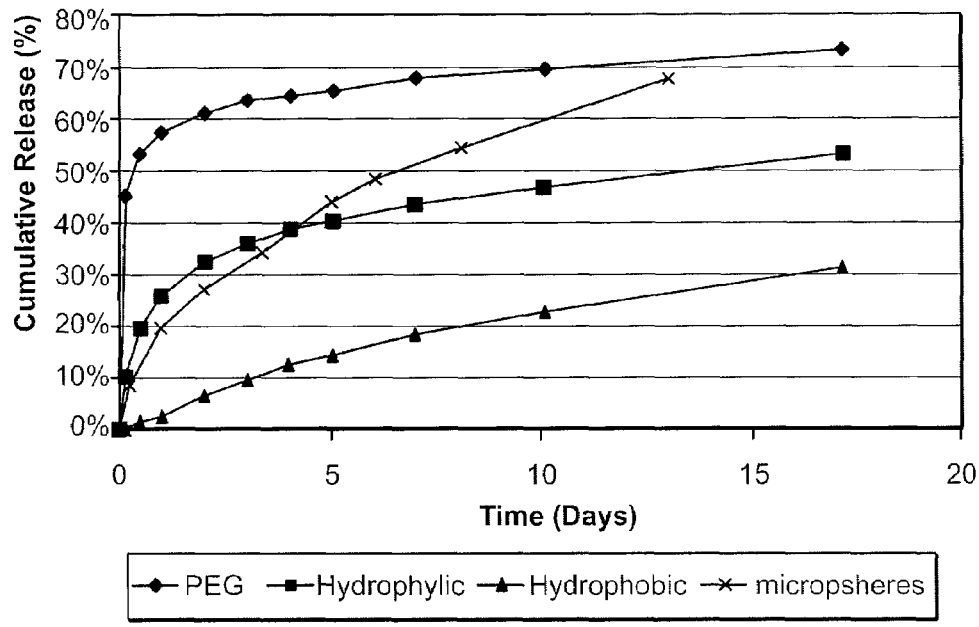
FIG. 13A shows the release rate of p(5% DT, DTE succinate) ketoprofen-containing microparticles in three different paste formulations.
Figure 13B:
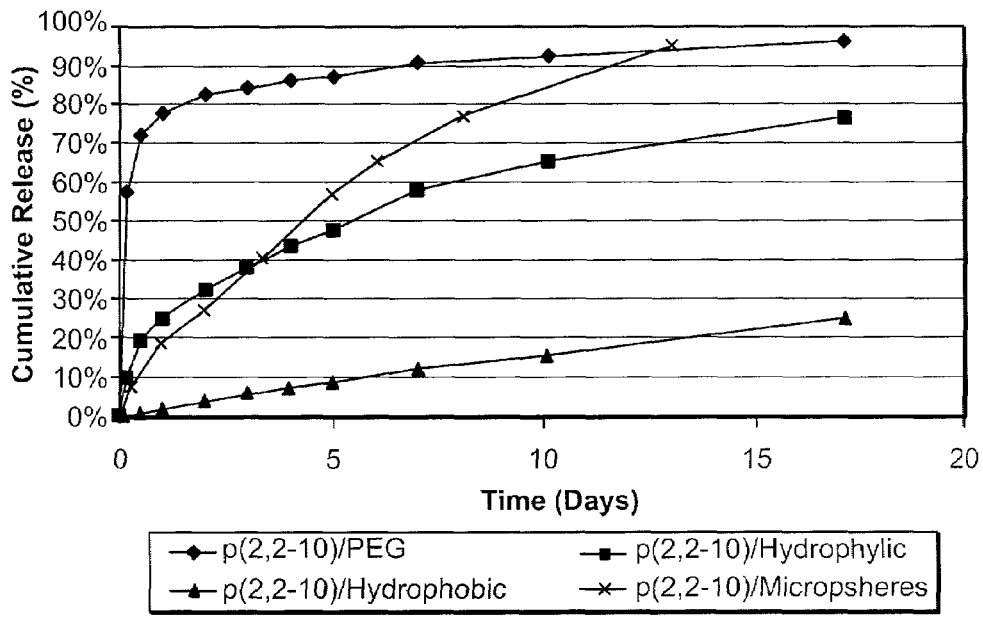
FIG. 13B shows the release rate of p(10% DT, DTE succinate) ketoprofen-containing microparticles in three different paste formulations.
Figure 13C:
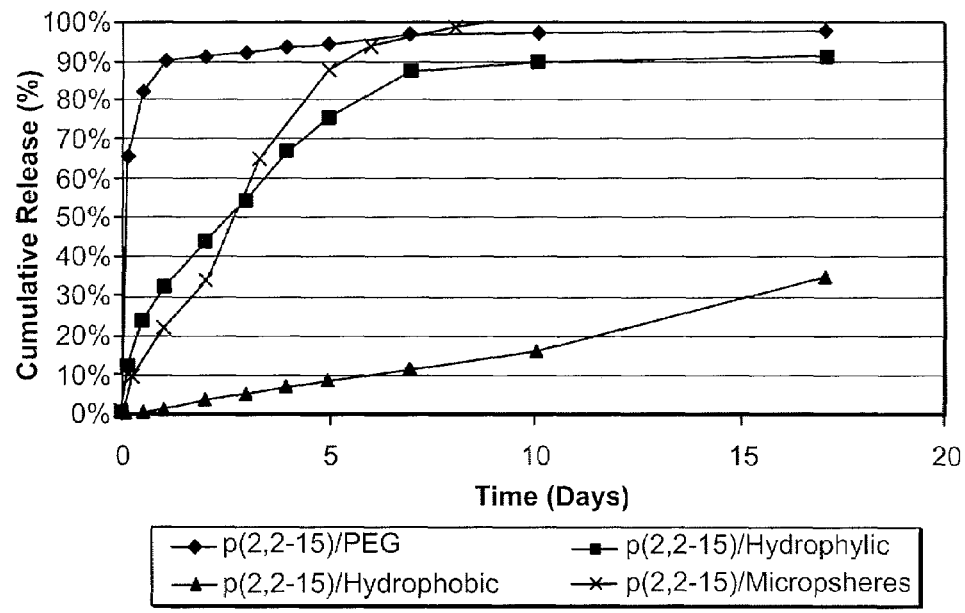
FIG. 13C shows the release rate of p(15% DT, DTE succinate) ketoprofen-containing microparticles in three different paste formulations. Symbols for each are (*) microparticle control, (♦) PEG paste, (▲) hydrophobic paste and (■) hydrophilic paste.

Between 10 to 25 mg paste was transferred to 50 ml polypropylene centrifuge tubes and 20 ml of PBS (pH 7.4, 0.01 M) was added. The tubes were capped and placed in a 37° C. incubator shaker and shaken at 200 rpm. At periodic intervals, 10 ml of buffer was removed for analysis and 10 ml fresh buffer added. The samples were analyzed for ketoprofen using the HPLC method described in Example 1. The % cumulative release is shown in FIG. 13A for p(5% DT, DTE succinate) pastes, in FIG. 13B for p(10% DT, DTE succinate) pastes and in FIG. 17C for p(15% DT, DTE succinate) pastes. Pure microparticles were used as a control.

Example 8

Naproxen Release

Naproxen was formulated at 20% loading in a matrix of p(10% DT, DTE succinate) by solvent casting from methylene chloride and assessed for long-term release. Unlike the ketoprofen films, these films were not clear. Naproxen was measured by HPLC, analogously to the method described above for ketoprofen.

Figure 14:
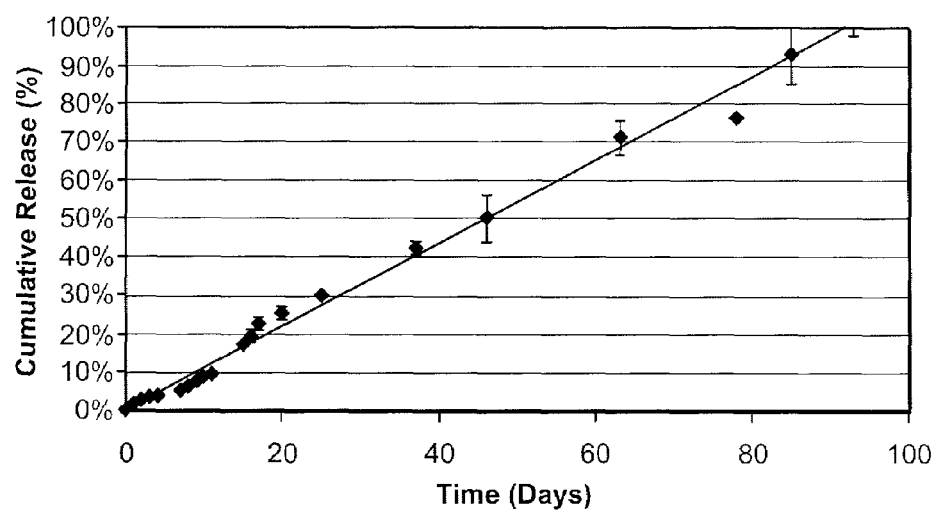
FIG. 14 shows the rate of release of naproxen from p(10% DT, DTE succinate).

Naproxen was released in a slow but linear fashion (i.e., with zero order kinetics) from p(10% DT, DTE succinate). Release was complete in about 3 months, with 1% drug released per day (FIG. 14). These results indicate that polyarylates can be used for the long-term delivery of naproxen.

The results with naproxen indicate that polyarylates are a general carrier that can be used for the long-term delivery of a variety of NSAIDs, and are not limited to the delivery of ketoprofen.

We claim:

1. A formulation comprising a tyrosine-derived polyarylate having at least one p(DT-succinate) group and an NSAID physically admixed, dissolved, dispersed, or embedded within said tyrosine-derived polyarylate, wherein said tyrosine-derived polyarylate and said NSAID form a homogeneous solid matrix, and wherein said formulation provides a burst-free, sustained release of said NSAID.

2. The formulation according to claim 1, wherein when measured in vitro under physiological conditions at 37° C., amounts in said formulation release less than about 50% of said NSAID within 24 hours and continue to release said NSAID for at least 3 to 5 days.

3. The formulation of claim 1, wherein said NSAID is a propionic acid-derived NSAID.

4. The formulation according to claim 1, wherein said NSAID is ketoprofen or naproxen.

5. The formulation of claim 1, wherein said formulation is prepared as a solvent-cast film, a solvent-free film (e.g., compression molded), microparticles or microspheres.

6. The formulation of claim 1, further comprising an ointment base that is formulated into a paste.

7. The formulation of claim 1, wherein said formulation comprises an amount of NSAID between about 10 to about 40% by weight.

8. The formulation of claim 1, wherein said release is linear.

9. The formulation of claim 1, wherein said formulation is in the form of microparticles.

10. The formulation of claim 9, wherein the microparticles have a size ranging from about 212 µm to about 425 µm.

11. The formulation of claim 9, wherein the microparticles have a size ranging from about 425 µm to about 500 µm.

12. The formulation of claim 9, wherein the microparticles have a size greater than 500 µm.

13. A formulation comprising a tyrosine-derived polyarylate and an NSAID physically admixed, dissolved, dispersed, or embedded within said tyrosine-derived polyarylate, wherein said tyrosine-derived polyarylate and said NSAID form a homogeneous solid matrix, wherein said formulation provides a burst-free, sustained release of said NSAID, wherein said tyrosine-derived polyarylate is comprised of a mixture of p(DTE-succinate) and p(DT-succinate) monomers.

* * * * *